US009388439B2

(12) United States Patent
Schaffer et al.

(10) Patent No.: US 9,388,439 B2
(45) Date of Patent: Jul. 12, 2016

(54) ACETYLTRANSFERASE FROM WICKERHAMOMYCES CIFERRII

(71) Applicant: EVONIK INDUSTRIES AG, Essen (DE)

(72) Inventors: Steffen Schaffer, Herten (DE); Mike Farwick, Essen (DE); Heiko Andrea, Marl (DE); Tim Koehler, Dorsten (DE); Daniel Wolff, Bochum (DE); Frank ter Veld, Wuppertal (DE); Ansgar Poetsch, Bochum (DE); Eckhard Boles, Darmstadt (DE); Christoph Schorsch, Frankfurt am Main (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/391,480

(22) PCT Filed: Mar. 13, 2013

(86) PCT No.: PCT/EP2013/055092
§ 371 (c)(1),
(2) Date: Oct. 9, 2014

(87) PCT Pub. No.: WO2013/152913
PCT Pub. Date: Oct. 17, 2013

(65) Prior Publication Data
US 2015/0118721 A1    Apr. 30, 2015

(30) Foreign Application Priority Data
Apr. 11, 2012   (DE) .......................... 10 2012 007 491

(51) Int. Cl.
C12N 9/10          (2006.01)
C12P 13/00         (2006.01)
C12P 7/64          (2006.01)
C07H 21/04         (2006.01)
C12P 13/02         (2006.01)

(52) U.S. Cl.
CPC ............... *C12P 13/02* (2013.01); *C12N 9/1025* (2013.01); *C12N 9/1029* (2013.01); *C12P 13/001* (2013.01)

(58) Field of Classification Search
None
See application file for complete search history.

(56) References Cited

U.S. PATENT DOCUMENTS

| | | |
|---|---|---|
| 4,601,893 A | 7/1986 | Cardinal |
| 5,910,425 A | 6/1999 | De Boer et al. |
| 8,372,595 B2 | 2/2013 | Schaffer et al. |
| 2007/0003509 A1 | 1/2007 | Farwick et al. |
| 2008/0249073 A1 | 10/2008 | Farwick et al. |
| 2010/0184733 A1 | 7/2010 | Korevaar et al. |
| 2014/0199736 A1 | 7/2014 | Kohler et al. |

FOREIGN PATENT DOCUMENTS

| | | |
|---|---|---|
| DE | 10031999 A1 | 4/2001 |
| DE | 102011110959 A1 | 2/2013 |
| EP | 0472869 A2 | 3/1992 |
| JP | H10229891 A | 9/1998 |
| WO | 95/12683 | 5/1995 |
| WO | WO 9615246 A1 | 5/1996 |
| WO | WO 2006/048458 A2 | 5/2006 |
| WO | WO 2007131720 A1 | 11/2007 |

OTHER PUBLICATIONS

International Search Report dated Jul. 12, 2013 issued in PCT/EP2013/055092.
De Schutter, Kristof, "Genome sequence of the recombinant protein production host Pichia pastoris", Nature Biotechnology (Jun. 2009), vol. 27, No. 6, pp. 561-566.
Database UniProt (Online), SubName: Full=N-acetyltransferase, confers resistance to the sphingolipid biosynthesis inhibitor myriocin (ISP-1), XP002696842, retrieved from EBI accession No. UNIPROT:C4R717, Database accession No. C4R717.
Kueberl, Andreas et al., "High-quality genome sequence of Pichia pastoris CBS7435", Journal of Biotechnology (2011), vol. 154, pp. 312-320.
Schorsch, Christoph et al., "High-level production of tetraacetyl phytosphingosine (TAPS) by combined genetic engineering of sphingoid base biosynthesis and L-serine availability in the non-conventional yeast Pichia ciferrii", Metabolic Engineering (2012), vol. 14, pp. 172-184.
Boergel, Daniel et al., "Metabolic engineering of the non-conventional yeast Pichia ciferrii for production of rare sphingoid bases", Metabolic Engineering (2012), vol. 14, pp. 412-426.
Schneider, Jessica et al., "Draft Genome Sequence of Wickerhamomyces ciferrii NRRL Y-1031 F-60-10", Eukaryotic Cell (Dec. 1, 2012), vol. 11, No. 12, pp. 1582-1583.
Database UniProt (Online), "Subname: Full=N-acetyltransferase SLI1; EC=2.3.1-;", XP002696843, retrieved from EBI accession No. UNITPROT:K0KN92, Database accession No. K0KN92.
Barenholz, Yechezkel et al., "Identification of the enzymatic lesions responsible for the accumulation of acetylated sphingosine bases in the yeast Hansenula ciferri", Biochimica et Biophysica Acta (1973), vol. 306, pp. 341-345.
Barenholz, Yechezkel et al., "Long Chain Base-Acetyl Coenzyme A Acetyltransferase from the Microsomes of Hansenula ciferri", The Journal of Biological Chemistry (Nov. 10, 1972), vol. 247, No. 21, pp. 6834-6839.
Barenholz, Yechezkel et al., "The Metabolic Basis for the Accumulation of Acetylated Sphingosine Bases in the Yeast Hansenula Ciferri", Biochimica Et Biophysica Acta (1971), vol. 248, pp. 458-465.
Buede, Rebecca et al., "Cloning and Characterization of LCB1, a *Saccharomyces* Gene Required for Biosynthesis of the Long-Chain Base Component of Sphingolipids", Journal of Bacteriology (Jul. 1991), vol. 173, No. 14, pp. 4325-4332.

(Continued)

*Primary Examiner* — Iqbal H Chowdhury
(74) *Attorney, Agent, or Firm* — Scully, Scott, Murphy & Presser, P.C.

(57) ABSTRACT

The invention relates to novel enzymes that provide acetylated sphingoid bases.

7 Claims, No Drawings

(56) References Cited

OTHER PUBLICATIONS

Dissertation of Daniel Boegel from Muenster: Untersuchungen zur Sphingolipid-Biosynthese in der Hefe Pichia ciferii, Johann Wolfgang Goethe-Universitaet in Frankfurt am Main, 2007, S.28, 63, 82, 116-117 u.185.

Altschul, S., et al., "Basic Local Alignment Search Tool", Journal of Molecular Biology,1990, vol. 215, pp. 403-410.

Barenholz, Y. and Gatt, S, "Long Chain Base-Acetyl Coenzyme A Acetyltransferase from the Microsomes of Hansenula ciferri", The Journal of Biological Chemistry, 1972, issue of Nov. 10, 247 (21): 6827-6833.

Becker, J. and Boles, E., "A Modified *Saccharomyces cerevisiae* Strain That Consumes L-Arabinose and Produces Ethanol", Applied and Environmental Microbiology, Jul. 2003, 69(7): 4144-4150.

Ben-Bassat, A., et al., "Processing of the Initiation Methionine from Proteins: Properties of the *Escherichia coli* Methionine Aminopeptidase and Its Gene Structure", Journal of Bacteriology, Feb. 1987, 169(2):751-757.

Bjerve, K.S., et al., "The Selective Loss of Lysophospholipids in Some Commonly Used Lipid-Extraction Procedures", Anal. Biochem., 1974, vol. 58, pp. 238-245.

Devereux, J., et al., "A comprehensive set of sequence analysis programs for the VAX", Nucleic Acid Research, 1984, 12(1):387-395, Genetics Computer Group, University of Wisconsin, Medicine (WI).

Donahue, J.L., et al., "Purification and Characterization of glpX-Encoded Fructose1,6-Bisphosphatase, a New Enzyme of the Glycerol 3-Phosphate Regulon of *Escherichia coli*", Journal of Bacteriology, Oct. 2000, 182 (19): 5624-5627.

Dower, W.J., et al., "High efficiency transformation of *E. coli* by high voltage electroporation", Nucleic Acids Research, 1988,16(3): 6127-6145.

Dunican, L.K. and Shivnan, E., "High Frequency Transformation of Whole Cells of Amino Acid Producing Coryneform Bacteria Using High Voltage Electroporation", Bio/Technology, Oct. 1989, 7: 1067-1070.

Eikmanns, B.J., et al., "A family of Corynebacterium glutamicum/*Escherichia coli* shuttle vectors for cloning, contrilled gene expression, and promoter probing", 1991, Gene 102, 93-98.

Freedberg, W.B. and Lin, E.C.C., "Three Kinds of Controls Affecting the Expression of the glp Regulon in *Escherichia coli*", Journal of Bacteriology, Sep. 1973, 115 (3): 816-823.

Gietz, R.D. and Schiestl, R.H., "High-efficiency yeast transformation using the LiAc/SS carrier DNA/PEG method", Nature Protocols, 2007, 2(1): 31-34.

Goeddel, D. V., "Systems for Heterologous Gene Expression", Methods in Enzymology, 1990, vol. 185, pp. 3-7.

Guerrero, C., et al., "Directed mutagenesis of a regulatory palindromic sequence upstream from the Brevibacterium lactofermentum tryptophan operon", Gene, 1994, vol. 138, pp. 35-41.

Hamacher, T., et al., "Characterization of the xylose-transporting properties of yeast hexose transporters and their influence on xylose utilization", Microbiology, 2002, vol. 148, pp. 2783-2788.

Hermann, T., et al., "Proteome analysis of Corynebacterium glutamicum", Electrophoresis, 2001, vol. 22, pp. 1712-1723.

Hochuli, E., et al., "Genetic Approach to Facilitate Purification of Recombinant Proteins with a Novel Metal Chelate Adsorbent", Bio/Technology, Nov. 1988, vol. 6, pp. 1321-1325.

Jensen, P.R. and Hammer, K., "Artificial Promoters for Metabolic Optimization" , Biotechnology and Bioengineering, Apr. 20 and May 5, 1998, vol. 58, Nos. 2 & 3, pp. 191-195.

LaBarre, J., et al., "Gene Replacement, Integration, and Amplification at the gdhA Locus of Corynebacterium glutamicum", Journal of Bacteriology, Feb. 1993, 175(4):1001-1007.

Lohaus, C. and Meyer, H.E., "Proteomforschung", Biospektrum, 1999, 5: 32-39.

Lottspeich, F., "Proteomanalyse-ein Weg zur Funktionsanalyse von Proteinen", Angewandte Chemie, 1999, vol. 111: pp. 2630-2647.

Malumbres, M., et al., "Codon Preference in Corynebacteria", Gene,1993, vol. 134, pp. 15-24.

Martin, J.F., et al., "Cloning Systems in Amino Acid-Producing Corynebacteria", Bio/Technology, Feb. 1987, vol. 5, 137-146.

Mösch, H. and Fink, G.R., "Dissection of Filamentous Growth by Transposon Mutagenesis in *Saccharomyces cerevisiae*", Genetics, Mar. 1997, vol. 145, pp. 671-684.

Murray, M.G. and Thompson, W.F., "Rapid isolation of high molecular weight DNA", Nucleic Acids Research, 1980, 8(19): 4321-4325.

Oldenburg, K.R., et al., "Recombination-mediated PCR-directed plasmid construction in vivo in yeast", Nucleic Acids Research, 1997, 25(2): 451-452.

O'Regan, M., et al., "Cloning and nucleotide sequence of the phosphoenolpyruvate carboxylase-coding gene of Corynebacterium ATCC13032", Gene, 1989, vol. 77, pp. 237-251.

Ray, W.K., et al., "Characterization of a 12-Kilodalton Rhodanese Encoded by glpE of *Escherichia coli* and Its Interaction with Thioredoxin", Journal of Bacteriology, Apr. 2000, 182(8): 2277-2284.

Reinscheid, D.J., et al., "Stable Expression of hom-1-thrB in Corynebacterium glutamicum and Its Effect on the Carbon Flux to Threonine and Related Amino Acids", Applied and Environmental Microbiology, Jan. 1994, 60(1):126-132.

Rodriguez, R.L. and Denhardt, D. T., "Vectors: a survey of molecular cloning vectors and their uses", Butterworth, Stoneham, 1988, pp. 179-203.

Sahin-Toth, M., et al., "Cysteine scanning mutagenesis of the N-terminal 32 amino acid residues in the lactose permease of *Escherichia coli*", 1994, Protein Sciences, vol. 3, pp. 240-247.

Schäfer, A., et al., "Increased Fertility of Corynebacterium glutamicum Recipeints in Intergeneric Matings with *Escherichia coli* after Stress Exposure", Applied and Environmental Microbiology, Feb. 1994, 60(2): 756-759.

Schorsch, C., et al., "Knockout of the DNA ligase IV homolog gene in the sphingoid base producing yeast Pichia ciferrii signifcantly increases gene targeting efficiency", Current Genetics, 2009, vol. 55, pp. 381-389.

Schwarzer, A. and Pühler, A.,"Manipulation of Corynebacterium Glutamicum by Gene Disruption and Replacement", Bio/Technology, Jan. 1991, vol. 9, pp. 84-87.

Tauch, A., et al., "Corynebacterium glutamicum DNA is subjected to methylation-restriction in *Escherichia coli*", FEMS Microbiology Letters 123, 1994, vol. 123, pp. 343-347.

Thierbach, G., et al., Transformation of spheroplasts and protoplasts of Corynebacterium glutamicum, Applied Microbiology and Biotechnology, 1988, vol. 29, pp. 356-362.

Tsuchiya, M and Morinaga, Y., "Genetic Control Systems of *Escherichia coli* Can Confer Inducible Expression of Cloned Genes in Coryneform Bacteria", Bio/Technology, Apr. 1988, vol. 6, pp. 428-430.

Wickerham, L.J. and Stodola, F.H., "Formation of Extracellular Sphingolipides by Microorganisms", Journal of Bacteriology, 1960, vol. 80, pp. 484-491.

Wilson, M.J., et al., "Analysis of Promoters Recognized by PvdS, an Extracytoplasmic-Function Sigma Factor Protein from Pseudomonas aeruginosa", Journal of Bacteriology, Mar. 2001, 183(6): 2151-2155.

Barenholz Y. et al., "Acetylation of Sphingosine Bases and Long-Chain Amines by Cell-Free Preparations of Hansenula Ciferri", Biochemical and Biophysical Research Communications 35(5):676-680 (1969).

Bögel D., "Untersuchungen Zur Sphingolipid-Biosynthese in Der Hefe Pichia Ciferrii", Johann Wolfgang Goethe Universität, Seiten 28-63, Dissertation (2007), together with a machine partial English-language translation for relevant pp. 28, 63, 82, 116-1178 and 185 according to the European Office Action.

European Office Action dated Aug. 4, 2015 received in European Patent Application No. 13 709 4223.

SEQUENCE LISTING

```
<160> NUMBER OF SEQ ID NOS: 12

<210> SEQ ID NO 1
<211> LENGTH: 1326
<212> TYPE: DNA
<213> ORGANISM: Pichia ciferrii
<220> FEATURE:
<221> NAME/KEY: CDS
<222> LOCATION: (1)..(1326)

<400> SEQUENCE: 1 atg gtg gct gga cca aac aaa gat ctt gaa aac ctg gaa cgt atg atg      48
Met Val Ala Gly Pro Asn Lys Asp Leu Glu Asn Leu Glu Arg Met Met
1               5                   10                  15 tac tgg aag acc act ttg aaa gct tgg tca tgt ttc ctt gtt ggt gct      96
Tyr Trp Lys Thr Thr Leu Lys Ala Trp Ser Cys Phe Leu Val Gly Ala
                20                  25                  30 aaa tta aac gaa aaa tta gaa aca gat gat att tta aaa ggt atc cac     144
Lys Leu Asn Glu Lys Leu Glu Thr Asp Asp Ile Leu Lys Gly Ile His
            35                  40                  45 aaa tta ttc acg ttg agg gtt cag tta cgt ttg aat gtt ttc caa tat     192
Lys Leu Phe Thr Leu Arg Val Gln Leu Arg Leu Asn Val Phe Gln Tyr
        50                  55                  60 cct aaa aaa agg ttt gtt acc gaa gag ata aat ggt tgg tct gat gat     240
Pro Lys Lys Arg Phe Val Thr Glu Glu Ile Asn Gly Trp Ser Asp Asp
65                  70                  75                  80 ttt gtt gat ttt gtc gat tat cca act gat gat ttt gat att att gaa     288
Phe Val Asp Phe Val Asp Tyr Pro Thr Asp Asp Phe Asp Ile Ile Glu
                85                  90                  95 gct ttt aaa caa caa cat aat caa tat ttt gaa ttg ggt gtt caa aag     336
Ala Phe Lys Gln Gln His Asn Gln Tyr Phe Glu Leu Gly Val Gln Lys
                100                 105                 110 cct tta tgg aaa ttg gtt gta ttg aac cat caa tat tta gtt att ctt     384
```

```
          Pro Leu Trp Lys Leu Val Val Leu Asn His Gln Tyr Leu Val Ile Leu
                      115                 120                 125 tgt gat cat acc tta tat gat ggg aac act gca ctt tat ata tgt gag        432
Cys Asp His Thr Leu Tyr Asp Gly Asn Thr Ala Leu Tyr Ile Cys Glu
            130                 135                 140 gat ttg atc aca ata ttg aat gat cgt gat atc cca gtt gat aga att        480
Asp Leu Ile Thr Ile Leu Asn Asp Arg Asp Ile Pro Val Asp Arg Ile
145                 150                 155                 160 cca gat att aaa cca tat cat gat cta tta aaa cca aaa ctt gga cat        528
Pro Asp Ile Lys Pro Tyr His Asp Leu Leu Lys Pro Lys Leu Gly His
                165                 170                 175 aca atc aaa act gtc atc caa act ttt gca cca aaa tgg gct tat cct        576
Thr Ile Lys Thr Val Ile Gln Thr Phe Ala Pro Lys Trp Ala Tyr Pro
            180                 185                 190 tta gtt aat ctg att tat aga cca aaa agt gaa ttt gaa act ggt gca        624
Leu Val Asn Leu Ile Tyr Arg Pro Lys Ser Glu Phe Glu Thr Gly Ala
        195                 200                 205 tat gat gat tgg gga gta act cat aaa att gaa aga aca aca aat aaa        672
Tyr Asp Asp Trp Gly Val Thr His Lys Ile Glu Arg Thr Thr Asn Lys
210                 215                 220 tta aag cac tta att aca ata act aat gaa gaa ttt tcc ata att aaa        720
Leu Lys His Leu Ile Thr Ile Thr Asn Glu Glu Phe Ser Ile Ile Lys
225                 230                 235                 240 aaa tta aca aaa tca cat ggt gta aat ttc aca gca ttt tgg gca tat        768
Lys Leu Thr Lys Ser His Gly Val Asn Phe Thr Ala Phe Trp Ala Tyr
                245                 250                 255 atc aat gtt ctt gca gtt gca caa ttg gga aag tca gct gtt gat tta        816
Ile Asn Val Leu Ala Val Ala Gln Leu Gly Lys Ser Ala Val Asp Leu
            260                 265                 270 tca att cca ttc aat atg aga acc aat tta tta cca cca gaa tat tta        864
Ser Ile Pro Phe Asn Met Arg Thr Asn Leu Leu Pro Pro Glu Tyr Leu
        275                 280                 285 aga tgg tat ggt tta tta gtt tca cat gtt act tta aat gta cat acc        912
Arg Trp Tyr Gly Leu Leu Val Ser His Val Thr Leu Asn Val His Thr
290                 295                 300 aaa gtt gat cat gat tca att gac tgg gat ttt gtt aga ttt tta aat        960
Lys Val Asp His Asp Ser Ile Asp Trp Asp Phe Val Arg Phe Leu Asn
305                 310                 315                 320 ggt agt gtt gca cat aaa tac caa gta aaa caa tca caa atg ctt gga       1008
Gly Ser Val Ala His Lys Tyr Gln Val Lys Gln Ser Gln Met Leu Gly
                325                 330                 335 atg att aaa tat gtt agt gct cgt gga ctt att gaa tca gct tta aaa       1056
Met Ile Lys Tyr Val Ser Ala Arg Gly Leu Ile Glu Ser Ala Leu Lys
            340                 345                 350 tca cca aga aaa ggt gga tta gaa gtt tca aac ttg gga ttg aga gtc       1104
Ser Pro Arg Lys Gly Gly Leu Glu Val Ser Asn Leu Gly Leu Arg Val
        355                 360                 365 gat cca gat ggt gaa tca tgg aaa aaa tat acc cct gaa gaa ttt ttc       1152
Asp Pro Asp Gly Glu Ser Trp Lys Lys Tyr Thr Pro Glu Glu Phe Phe
370                 375                 380 ttt tct ttg cca aat gat ctt tca ggt tat aat gtt tca aat gct gtg       1200
Phe Ser Leu Pro Asn Asp Leu Ser Gly Tyr Asn Val Ser Asn Ala Val
385                 390                 395                 400 att tca agt aaa act aaa aca aat att att tta gac ggt gtt cca gaa       1248
Ile Ser Ser Lys Thr Lys Thr Asn Ile Ile Leu Asp Gly Val Pro Glu
                405                 410                 415 ttt gca aat gaa ttt cca acg tat gca aat aac gtt gaa aca att ttg       1296
Phe Ala Asn Glu Phe Pro Thr Tyr Ala Asn Asn Val Glu Thr Ile Leu
            420                 425                 430
```

```
            aga aat gca atc aat ggg tat tat gaa taa                    1326
            Arg Asn Ala Ile Asn Gly Tyr Tyr Glu
                435                 440

<210> SEQ ID NO 2
<211> LENGTH: 441
<212> TYPE: PRT
<213> ORGANISM: Pichia ciferrii

<400> SEQUENCE: 2

Met Val Ala Gly Pro Asn Lys Asp Leu Glu Asn Leu Glu Arg Met Met
1               5                   10                  15

Tyr Trp Lys Thr Thr Leu Lys Ala Trp Ser Cys Phe Leu Val Gly Ala
            20                  25                  30

Lys Leu Asn Glu Lys Leu Glu Thr Asp Asp Ile Leu Lys Gly Ile His
        35                  40                  45

Lys Leu Phe Thr Leu Arg Val Gln Leu Arg Leu Asn Val Phe Gln Tyr
    50                  55                  60

Pro Lys Lys Arg Phe Val Thr Glu Glu Ile Asn Gly Trp Ser Asp Asp
65                  70                  75                  80

Phe Val Asp Phe Val Asp Tyr Pro Thr Asp Asp Phe Asp Ile Ile Glu
                85                  90                  95

Ala Phe Lys Gln Gln His Asn Gln Tyr Phe Glu Leu Gly Val Gln Lys
            100                 105                 110

Pro Leu Trp Lys Leu Val Val Leu Asn His Gln Tyr Leu Val Ile Leu
        115                 120                 125

Cys Asp His Thr Leu Tyr Asp Gly Asn Thr Ala Leu Tyr Ile Cys Glu
    130                 135                 140

Asp Leu Ile Thr Ile Leu Asn Asp Arg Asp Ile Pro Val Asp Arg Ile
145                 150                 155                 160

Pro Asp Ile Lys Pro Tyr His Asp Leu Leu Lys Pro Lys Leu Gly His
                165                 170                 175

Thr Ile Lys Thr Val Ile Gln Thr Phe Ala Pro Lys Trp Ala Tyr Pro
            180                 185                 190

Leu Val Asn Leu Ile Tyr Arg Pro Lys Ser Glu Phe Glu Thr Gly Ala
        195                 200                 205

Tyr Asp Asp Trp Gly Val Thr His Lys Ile Glu Arg Thr Thr Asn Lys
    210                 215                 220

Leu Lys His Leu Ile Thr Ile Thr Asn Glu Glu Phe Ser Ile Ile Lys
225                 230                 235                 240

Lys Leu Thr Lys Ser His Gly Val Asn Phe Thr Ala Phe Trp Ala Tyr
                245                 250                 255

Ile Asn Val Leu Ala Val Ala Gln Leu Gly Lys Ser Ala Val Asp Leu
            260                 265                 270

Ser Ile Pro Phe Asn Met Arg Thr Asn Leu Leu Pro Pro Glu Tyr Leu
        275                 280                 285

Arg Trp Tyr Gly Leu Leu Val Ser His Val Thr Leu Asn Val His Thr
    290                 295                 300

Lys Val Asp His Asp Ser Ile Asp Trp Asp Phe Val Arg Phe Leu Asn
305                 310                 315                 320

Gly Ser Val Ala His Lys Tyr Gln Val Lys Gln Ser Gln Met Leu Gly
                325                 330                 335

Met Ile Lys Tyr Val Ser Ala Arg Gly Leu Ile Glu Ser Ala Leu Lys
            340                 345                 350

Ser Pro Arg Lys Gly Gly Leu Glu Val Ser Asn Leu Gly Leu Arg Val
```

-continued

```
                355                 360                 365
Asp Pro Asp Gly Glu Ser Trp Lys Lys Tyr Thr Pro Glu Glu Phe Phe
    370                 375                 380

Phe Ser Leu Pro Asn Asp Leu Ser Gly Tyr Asn Val Ser Asn Ala Val
385                 390                 395                 400

Ile Ser Ser Lys Thr Lys Thr Asn Ile Ile Leu Asp Gly Val Pro Glu
                405                 410                 415

Phe Ala Asn Glu Phe Pro Thr Tyr Ala Asn Asn Val Glu Thr Ile Leu
            420                 425                 430

Arg Asn Ala Ile Asn Gly Tyr Tyr Glu
        435                 440
```

<210> SEQ ID NO 3
<211> LENGTH: 1431
<212> TYPE: DNA
<213> ORGANISM: Pichia ciferrii
<220> FEATURE:
<221> NAME/KEY: CDS
<222> LOCATION: (1)..(1431)

<400> SEQUENCE: 3

```
atg tca ttt aaa tat atc aat caa aat gat tca aaa tca tta tca aat        48
Met Ser Phe Lys Tyr Ile Asn Gln Asn Asp Ser Lys Ser Leu Ser Asn
1               5                   10                  15 tta aaa tat aaa tta tca aaa aat cat gca aga caa atg ggt ttt tta        96
Leu Lys Tyr Lys Leu Ser Lys Asn His Ala Arg Gln Met Gly Phe Leu
                20                  25                  30 gaa gat ttt ttt gca att tta caa cgt caa aaa atg tat aaa tca ttt       144
Glu Asp Phe Phe Ala Ile Leu Gln Arg Gln Lys Met Tyr Lys Ser Phe
            35                  40                  45 ttc gtt atg tgt aaa tat aat gaa aaa att gat gat ttt aaa att tta       192
Phe Val Met Cys Lys Tyr Asn Glu Lys Ile Asp Asp Phe Lys Ile Leu
        50                  55                  60 ttc cat tca tta aga tta tta ata tta aaa ttc cca ata tta gct tcc       240
Phe His Ser Leu Arg Leu Leu Ile Leu Lys Phe Pro Ile Leu Ala Ser
65                  70                  75                  80 aca ata att act caa aat gtt cca att aat ata aaa cct cgt cct tat       288
Thr Ile Ile Thr Gln Asn Val Pro Ile Asn Ile Lys Pro Arg Pro Tyr
                85                  90                  95 gat tat att caa att att gat gaa ata aaa ttt aat gat ttg gtt tgg       336
Asp Tyr Ile Gln Ile Ile Asp Glu Ile Lys Phe Asn Asp Leu Val Trp
                100                 105                 110 gat tta aga cct gaa tat tca aat tta tta caa gaa gat tta tta aat       384
Asp Leu Arg Pro Glu Tyr Ser Asn Leu Leu Gln Glu Asp Leu Leu Asn
            115                 120                 125 aaa tta aat gat tta att ata cca tat gaa gat aat aaa tta gtt tgg       432
Lys Leu Asn Asp Leu Ile Ile Pro Tyr Glu Asp Asn Lys Leu Val Trp
        130                 135                 140 aga tta gga atc ttg gat gat tat aca tta att ttt ata aca aat cat       480
Arg Leu Gly Ile Leu Asp Asp Tyr Thr Leu Ile Phe Ile Thr Asn His
145                 150                 155                 160 gtt tta cat gat gga ata tct ggt aaa aat att ttt aat gaa tta tca       528
Val Leu His Asp Gly Ile Ser Gly Lys Asn Ile Phe Asn Glu Leu Ser
                165                 170                 175 tta att ttt aat caa ttg gac ttg gat tct tta agt gat gat gat gat       576
Leu Ile Phe Asn Gln Leu Asp Leu Asp Ser Leu Ser Asp Asp Asp Asp
            180                 185                 190 atc gtg ttc aat tat tca caa gat cat ttg aat tta ggt gaa tta cca       624
Ile Val Phe Asn Tyr Ser Gln Asp His Leu Asn Leu Gly Glu Leu Pro
        195                 200                 205
```

```
aaa cct ata act gat ctt atg aat cat att cca tca att aaa tct tta      672
Lys Pro Ile Thr Asp Leu Met Asn His Ile Pro Ser Ile Lys Ser Leu
    210                 215                 220 cca aga tat att tat aat tca tta att gaa cca aaa ctt ttt tgt tca      720
Pro Arg Tyr Ile Tyr Asn Ser Leu Ile Glu Pro Lys Leu Phe Cys Ser
225                 230                 235                 240 tca act tta att caa ggt cat ctt aag aat att cat tat aga gtt aat      768
Ser Thr Leu Ile Gln Gly His Leu Lys Asn Ile His Tyr Arg Val Asn
            245                 250                 255 ata aat cca atg gaa tta tta aaa att aaa tca tta tca aaa aat          816
Ile Asn Pro Met Glu Leu Leu Lys Ile Lys Ser Leu Leu Ser Lys Asn
        260                 265                 270 agt ttc aat aat gtt aaa tta act tta aca cct ttc att caa tct att      864
Ser Phe Asn Asn Val Lys Leu Thr Leu Thr Pro Phe Ile Gln Ser Ile
    275                 280                 285 tgg aat tat act tta tat caa gat gaa tat tat aaa tca tca aaa tct      912
Trp Asn Tyr Thr Leu Tyr Gln Asp Glu Tyr Tyr Lys Ser Ser Lys Ser
290                 295                 300 tta tta ggt att gca gtg gat tct cgt caa ttt att aat aaa gat gaa      960
Leu Leu Gly Ile Ala Val Asp Ser Arg Gln Phe Ile Asn Lys Asp Glu
305                 310                 315                 320 caa gat tta tat aaa ttt ggt tta aat gta tca ggt ttt agt aaa att      1008
Gln Asp Leu Tyr Lys Phe Gly Leu Asn Val Ser Gly Phe Ser Lys Ile
            325                 330                 335 tcc aaa cca atg aaa tta att aca tgg aat aaa att aat caa att aat      1056
Ser Lys Pro Met Lys Leu Ile Thr Trp Asn Lys Ile Asn Gln Ile Asn
        340                 345                 350 caa gat tta aaa att tca tta aaa ttg aaa aaa cct tta tat tca atg      1104
Gln Asp Leu Lys Ile Ser Leu Lys Leu Lys Lys Pro Leu Tyr Ser Met
    355                 360                 365 ggt ata tta ggt tgg gat aaa atg att aaa aat aaa cat tta gat gtt      1152
Gly Ile Leu Gly Trp Asp Lys Met Ile Lys Asn Lys His Leu Asp Val
370                 375                 380 gat tta cca aaa att atg aat aaa aga aca ggt tca act ttt tca aat      1200
Asp Leu Pro Lys Ile Met Asn Lys Arg Thr Gly Ser Thr Phe Ser Asn
385                 390                 395                 400 att ggt ata atc cta aat aac agt gaa tca aat gat aaa ttt caa att      1248
Ile Gly Ile Ile Leu Asn Asn Ser Glu Ser Asn Asp Lys Phe Gln Ile
            405                 410                 415 att gat gca atg ttt aca caa cat ttt aat gtt cat ttt tat gat ttc      1296
Ile Asp Ala Met Phe Thr Gln His Phe Asn Val His Phe Tyr Asp Phe
        420                 425                 430 tca atc act gca att tct aca atg act ggt ggg tta aat att ata att      1344
Ser Ile Thr Ala Ile Ser Thr Met Thr Gly Gly Leu Asn Ile Ile Ile
    435                 440                 445 aca tca cca gaa tct att gga att gaa aat tta gaa aga att tgt aaa      1392
Thr Ser Pro Glu Ser Ile Gly Ile Glu Asn Leu Glu Arg Ile Cys Lys
450                 455                 460 aaa ttt cat gaa aat tta gtt tta tgt gat att aaa taa                  1431
Lys Phe His Glu Asn Leu Val Leu Cys Asp Ile Lys
465                 470                 475

<210> SEQ ID NO 4
<211> LENGTH: 476
<212> TYPE: PRT
<213> ORGANISM: Pichia ciferrii

<400> SEQUENCE: 4

Met Ser Phe Lys Tyr Ile Asn Gln Asn Asp Ser Lys Ser Leu Ser Asn
1               5                   10                  15
```

```
Leu Lys Tyr Lys Leu Ser Lys Asn His Ala Arg Gln Met Gly Phe Leu
         20                  25                  30

Glu Asp Phe Phe Ala Ile Leu Gln Arg Gln Lys Met Tyr Lys Ser Phe
             35                  40                  45

Phe Val Met Cys Lys Tyr Asn Glu Lys Ile Asp Phe Lys Ile Leu
 50                  55                  60

Phe His Ser Leu Arg Leu Leu Ile Leu Lys Phe Pro Ile Leu Ala Ser
 65                  70                  75                  80

Thr Ile Ile Thr Gln Asn Val Pro Ile Asn Ile Lys Pro Arg Pro Tyr
                 85                  90                  95

Asp Tyr Ile Gln Ile Ile Asp Glu Ile Lys Phe Asn Asp Leu Val Trp
                100                 105                 110

Asp Leu Arg Pro Glu Tyr Ser Asn Leu Leu Gln Glu Asp Leu Leu Asn
                115                 120                 125

Lys Leu Asn Asp Leu Ile Ile Pro Tyr Glu Asp Asn Lys Leu Val Trp
130                 135                 140

Arg Leu Gly Ile Leu Asp Asp Tyr Thr Leu Ile Phe Ile Thr Asn His
145                 150                 155                 160

Val Leu His Asp Gly Ile Ser Gly Lys Asn Ile Phe Asn Glu Leu Ser
                165                 170                 175

Leu Ile Phe Asn Gln Leu Asp Leu Asp Ser Leu Ser Asp Asp Asp
                180                 185                 190

Ile Val Phe Asn Tyr Ser Gln Asp His Leu Asn Leu Gly Glu Leu Pro
                195                 200                 205

Lys Pro Ile Thr Asp Leu Met Asn His Ile Pro Ser Ile Lys Ser Leu
        210                 215                 220

Pro Arg Tyr Ile Tyr Asn Ser Leu Ile Glu Pro Lys Leu Phe Cys Ser
225                 230                 235                 240

Ser Thr Leu Ile Gln Gly His Leu Lys Asn Ile His Tyr Arg Val Asn
                245                 250                 255

Ile Asn Pro Met Glu Leu Leu Lys Ile Lys Ser Leu Leu Ser Lys Asn
                260                 265                 270

Ser Phe Asn Asn Val Lys Leu Thr Leu Thr Pro Phe Ile Gln Ser Ile
                275                 280                 285

Trp Asn Tyr Thr Leu Tyr Gln Asp Glu Tyr Tyr Lys Ser Ser Lys Ser
        290                 295                 300

Leu Leu Gly Ile Ala Val Asp Ser Arg Gln Phe Ile Asn Lys Asp Glu
305                 310                 315                 320

Gln Asp Leu Tyr Lys Phe Gly Leu Asn Val Ser Gly Phe Ser Lys Ile
                325                 330                 335

Ser Lys Pro Met Lys Leu Ile Thr Trp Asn Lys Ile Asn Gln Ile Asn
                340                 345                 350

Gln Asp Leu Lys Ile Ser Leu Lys Leu Lys Pro Leu Tyr Ser Met
                355                 360                 365

Gly Ile Leu Gly Trp Asp Lys Met Ile Lys Asn Lys His Leu Asp Val
        370                 375                 380

Asp Leu Pro Lys Ile Met Asn Lys Arg Thr Gly Ser Thr Phe Ser Asn
385                 390                 395                 400

Ile Gly Ile Ile Leu Asn Asn Ser Glu Ser Asn Asp Lys Phe Gln Ile
                405                 410                 415

Ile Asp Ala Met Phe Thr Gln His Phe Asn Val His Phe Tyr Asp Phe
                420                 425                 430
```

```
Ser Ile Thr Ala Ile Ser Thr Met Thr Gly Gly Leu Asn Ile Ile Ile
        435                 440                 445

Thr Ser Pro Glu Ser Ile Gly Ile Glu Asn Leu Glu Arg Ile Cys Lys
    450                 455                 460

Lys Phe His Glu Asn Leu Val Leu Cys Asp Ile Lys
465                 470                 475

<210> SEQ ID NO 5
<211> LENGTH: 7483
<212> TYPE: DNA
<213> ORGANISM: Artificial Sequence
<220> FEATURE:
<223> OTHER INFORMATION: Vector

<400> SEQUENCE: 5
cgtcaggggg gcggagccta tggaaaaacg ccagcaacgc ggccttttta cggttcctgg      60
ccttttgctg gccttttgct cacatgttct ttcctgcgtt atcccctgat tctgtggata     120
accgtattac cgcctttgag tgagctgata ccgctcgccg cagccgaacg accgagcgca     180
gcgagtcagt gagcgaggaa gcggaagagc gcccaatacg caaaccgcct ctccccgcgc     240
gttggccgat tcattaatgc agctggcacg acaggtttcc cgactggaaa gcgggcagtg     300
agcgcaacgc aattaatgtg agttacctca ctcattaggc accccaggct ttacacttta     360
tgcttccggc tcctatgttg tgtggaattg tgagcggata caatttcac acaggaaaca      420 gctatgacca tgattacgcc aagcgcgcaa ttaaccctca ctaaagggaa caaaagctgg     480
agctcgtagg aacaatttcg ggcccctgcg tgttcttctg aggttcatct tttacatttg     540
cttctgctgg ataattttca gaggcaacaa ggaaaaatta gatggcaaaa agtcgtcttt     600
caaggaaaaa tccccaccat ctttcgagat cccctgtaac ttattggcaa ctgaaagaat     660 gaaaggagg aaaatacaaa atatactaga actgaaaaaa aaaagtata aatagagacg       720 atatatgcca atacttcaca atgttcgaat ctattcttca tttgcagcta ttgtaaaata     780 ataaacatc aagaacaaac aagctcaact tgtctttttct aagaacaaag aataaacaca     840
aaaacaaaaa gttttttaa ttttaatcaa aaagttaaca tgcatcacca tcaccatcac      900
actagtggat cccccgggct gcaggaattc gatatcaagc ttatcgatac cgtcgacctc     960
gagtcatgta attagttatg tcacgcttac attcacgccc tcccccccaca tccgctctaa    1020 ccgaaaagga aggagttaga caacctgaag tctaggtccc tatttatttt tttatagtta    1080
tgttagtatt aagaacgtta tttatatttc aaatttttct tttttttctg tacagacgcg    1140
tgtacgcatg taacattata ctgaaaacct tgcttgagaa ggttttggga cgctcgaagg    1200
ctttaatttg cggccggtac ccaattcgcc ctatagtgag tcgtattacg cgcgctcact    1260
ggccgtcgtt ttacaacgtc gtgactggga aaaccctggc gttacccaac ttaatcgcct    1320
tgcagcacat ccccctttcg ccagctggcg taatagcgaa gaggcccgca ccgatcgccc    1380
ttcccaacag ttgcgcagcc tgaatggcga atggcgcgac gcgccctgta gcggcgcatt    1440
aagcgcggcg ggtgtggtgg ttacgcgcag cgtgaccgct acacttgcca gcgccctagc    1500
gcccgctcct ttcgctttct tcccttcctt tctcgccacg ttcgccggct ttccccgtca    1560
agctctaaat cggggggctcc ctttagggtt ccgatttagt gctttacggc acctcgaccc    1620
caaaaaactt gattagggtg atggttcacg tagtgggcca tcgccctgat agacggtttt    1680
tcgccctttg acgttggagt ccacgttctt taatagtgga ctcttgttcc aaactggaac    1740
aacactcaac cctatctcgg tctattcttt tgatttataa gggattttgc cgatttcggc    1800
```

```
ctattggtta aaaaatgagc tgatttaaca aaaatttaac gcgaatttta acaaaatatt    1860
aacgtttaca atttcctgat gcggtatttt ctccttacgc atctgtgcgg tatttcacac    1920
cgcatatcga cggtcgagga gaacttctag tatatccaca tacctaatat tattgcctta    1980
ttaaaaatgg aatcccaaca attacatcaa aatccacatt ctcttcaaaa tcaattgtcc    2040
tgtacttcct tgttcatgtg tgttcaaaaa cgttatattt ataggataat tatactctat    2100
ttctcaacaa gtaattggtt gtttggccga gcggtctaag gcgcctgatt caagaaatat    2160
cttgaccgca gttaactgtg ggaatactca ggtatcgtaa gatgcaagag ttcgaatctc    2220
ttagcaacca ttatttttt cctcaacata acgagaacac acaggggcgc tatcgcacag    2280
aatcaaattc gatgactgga aatttttgt taatttcaga ggtcgcctga cgcatatacc    2340
tttttcaact gaaaaattgg gagaaaaagg aaaggtgaga ggccggaacc ggcttttcat    2400
atagaataga gaagcgttca tgactaaatg cttgcatcac aatacttgaa gttgacaata    2460
ttatttaagg acctattgtt ttttccaata ggtggttagc aatcgtctta ctttctaact    2520
tttcttacct tttacatttc agcaatatat atatatattt caaggatata ccattctaat    2580
gtctgcccct atgtctgccc ctaagaagat cgtcgttttg ccaggtgacc acgttggtca    2640
agaaatcaca gccgaagcca ttaaggttct taaagctatt tctgatgttc gttccaatgt    2700
caagttcgat ttcgaaaatc atttaattgg tggtgctgct atcgatgcta caggtgtccc    2760
acttccagat gaggcgctgg aagcctccaa gaaggttgat gccgttttgt taggtgctgt    2820
ggctggtcct aaatggggta ccggtagtgt tagacctgaa caaggtttac taaaaatccg    2880
taaagaactt caattgtacg ccaacttaag accatgtaac tttgcatccg actctctttt    2940
agacttatct ccaatcaagc cacaatttgc taaaggtact gacttcgttg ttgtcagaga    3000
attagtggga ggtatttact ttggtaagag aaaggaagac gatggtgatg gtgtcgcttg    3060
ggatagtgaa caatacaccg ttccagaagt gcaagaatc acaagaatgg ccgctttcat    3120
ggccctacaa catgagccac cattgcctat ttggtccttg gataaagcta atcttttggc    3180
ctcttcaaga ttatggagaa aaactgtgga ggaaaccatc aagaacgaat tccctacatt    3240
gaaggttcaa catcaattga ttgattctgc cgccatgatc ctagttaaga acccaaccca    3300
cctaaatggt attataatca ccagcaacat gtttggtgat atcatctccg atgaagcctc    3360
cgttatccca ggttccttgg gtttgttgcc atctgcgtcc ttggcctctt gccagacaa    3420
gaacaccgca tttggtttgt acgaaccatg ccacggttct gctccagatt gccaaagaa    3480
taaggttgac cctatcgcca ctatcttgtc tgctgcaatg atgttgaaat tgtcattgaa    3540
cttgcctgaa gaaggtaagg ccattgaaga tgcagttaaa aaggttttgg atgcaggtat    3600
cagaactggt gatttaggtg gttccaacag taccaccgaa gtcggtgatg ctgtcgccga    3660
agaagttaag aaaatccttg cttaaaaaga ttctcttttt ttatgatatt tgtacataaa    3720
ctttataaat gaaattcata atagaaacga cacgaaatta caaaatggaa tatgttcata    3780
gggtagacga aactatatac gcaatctaca tacatttatc aagaaggaga aaaggaggga    3840
tagtaaagga atacaggtaa gcaaattgat actaatggct caacgtgata aggaaaaaga    3900
attgcacttt aacattaata ttgacaagga ggagggcacc acacaaaag ttaggtgtaa    3960
cagaaaatca tgaaactacg attcctaatt tgatattgga ggattttctc taaaaaaaaa    4020
aaaatacaac aaataaaaaa cactcaatga cctgaccatt tgatggagtt taagtcaata    4080
ccttcttgaa gcatttccca taatggtgaa agttccctca agaattttac tctgtcagaa    4140
acggccttac gacgtagtcg atatggtgca ctctcagtac aatctgctct gatgccgcat    4200
```

```
agttaagcca gccccgacac ccgccaacac ccgctgacgc gccctgacgg gcttgtctgc   4260
tcccggcatc cgcttacaga caagctgtga ccgtctccgg gagctgcatg tgtcagaggt   4320
tttcaccgtc atcaccgaaa cgcgcgagac gaaagggcct cgtgatacgc ctattttat    4380
aggtaatgt catgataata atggtttctt agtatgatcc aatatcaaag gaatgatag     4440
cattgaagga tgagactaat ccaattgagg agtggcagca tatagaacag ctaaagggta   4500
gtgctgaagg aagcatacga taccccgcat ggaatgggat aatatcacag gaggtactag   4560
actacctttc atcctacata aatagacgca tataagtacg catttaagca taaacacgca   4620
ctatgccgtt cttctcatgt atatatatat acaggcaaca cgcagatata ggtgcgacgt   4680
gaacagtgag ctgtatgtgc gcagctcgcg ttgcatttc  ggaagcgctc gttttcggaa   4740
acgctttgaa gttcctattc cgaagttcct attctctaga aagtatagga acttcagagc   4800
gcttttgaaa accaaaagcg ctctgaagac gcactttcaa aaaccaaaa  acgcaccgga   4860
ctgtaacgag ctactaaaat attgcgaata ccgcttccac aaacattgct caaaagtatc   4920
tctttgctat atatctctgt gctatatccc tatataacct acccatccac ctttcgctcc   4980
ttgaacttgc atctaaactc gacctctaca ttttttatgt ttatctctag tattactctt   5040
tagacaaaaa aattgtagta agaactattc atagagtgaa tcgaaaacaa tacgaaaatg   5100
taaacatttc ctatacgtag tatatagaga caaaatagaa gaaaccgttc ataattttct   5160
gaccaatgaa gaatcatcaa cgctatcact ttctgttcac aaagtatgcg caatccacat   5220
cggtatagaa tataatcggg gatgccttta tcttgaaaaa atgcacccgc agcttcgcta   5280
gtaatcagta aacgcgggaa gtggagtcag gctttttta  tggaagagaa aatagacacc   5340
aaagtagcct tcttctaacc ttaacggacc tacagtgcaa aaagttatca agagactgca   5400
ttatagagcg cacaaaggag aaaaaaagta atctaagatg ctttgttaga aaaatagcgc   5460
tctcgggatg cattttgta  gaacaaaaaa gaagtataga ttctttgttg gtaaaatagc   5520
gctctcgcgt tgcattctg  ttctgtaaaa atgcagctca gattctttgt ttgaaaaatt   5580
agcgctctcg cgttgcattt ttgttttaca aaaatgaagc acagattctt cgttggtaaa   5640
atagcgcttt cgcgttgcat ttctgttctg taaaaatgca gctcagattc tttgtttgaa   5700
aaattagcgc tctcgcgttg cattttgtt  ctacaaaatg aagcacagat gcttcgttca   5760
ggtggcactt ttcggggaaa tgtgcgcgga acccctattt gtttatttt  ctaaatacat   5820
tcaaatatgt atccgctcat gagacaataa ccctgataaa tgcttcaata atattgaaaa   5880
aggaagagta tgagtattca acatttccgt gtcgcccta  ttccctttt  tgcggcattt   5940
tgccttcctg tttttgctca cccagaaacg ctggtgaaag taaaagatgc tgaagatcag   6000
ttgggtgcac gagtgggtta catcgaactg gatctcaaca gcggtaagat ccttgagagt   6060
tttcgccccg aagaacgttt tccaatgatg agcactttta aagttctgct atgtggcgcg   6120
gtattatccc gtattgacgc cgggcaagag caactcggtc gccgcataca ctattctcag   6180
aatgacttgg ttgagtactc accagtcaca gaaaagcatc ttacggatgg catgacagta   6240
agagaattat gcagtgctgc cataaccatg agtgataaca ctgcggccaa cttacttctg   6300
acaacgatcg gaggaccgaa ggagctaacc gcttttttgc acaacatggg ggatcatgta   6360
actcgccttg atcgttggga accggagctg aatgaagcca taccaaacga cgagcgtgac   6420
accacgatgc ctgtagcaat ggcaacaacg ttgcgcaaac tattaactgg cgaactactt   6480
actctagctt cccggcaaca attaatagac tggatggagg cggataaagt tgcaggacca   6540
```

|  |  |  |  |  |  |
|---|---|---|---|---|---|
| cttctgcgct | cggcccttcc | ggctggctgg | tttattgctg | ataaatctgg | agccggtgag | 6600 |
| cgtgggtctc | gcggtatcat | tgcagcactg | gggccagatg | gtaagccctc | ccgtatcgta | 6660 |
| gttatctaca | cgacggggag | tcaggcaact | atggatgaac | gaaatagaca | gatcgctgag | 6720 |
| ataggtgcct | cactgattaa | gcattggtaa | ctgtcagacc | aagtttactc | atatatactt | 6780 |
| tagattgatt | taaaacttca | ttttaattt | aaaaggatct | aggtgaagat | ccttttgat | 6840 |
| aatctcatga | ccaaaatccc | ttaacgtgag | ttttcgttcc | actgagcgtc | agaccccgta | 6900 |
| gaaaagatca | aaggatcttc | ttgagatcct | ttttttctgc | gcgtaatctg | ctgcttgcaa | 6960 |
| acaaaaaaac | caccgctacc | agcggtggtt | tgtttgccgg | atcaagagct | accaactctt | 7020 |
| tttccgaagg | taactggctt | cagcagagcg | cagataccaa | atactgtcct | tctagtgtag | 7080 |
| ccgtagttag | gccaccactt | caagaactct | gtagcaccgc | ctacatacct | cgctctgcta | 7140 |
| atcctgttac | cagtggctgc | tgccagtggc | gataagtcgt | gtcttaccgg | gttggactca | 7200 |
| agacgatagt | taccggataa | ggcgcagcgg | tcgggctgaa | cggggggttc | gtgcacacag | 7260 |
| cccagcttgg | agcgaacgac | ctacaccgaa | ctgagatacc | tacagcgtga | gctatgagaa | 7320 |
| agcgccacgc | ttcccgaagg | gagaaaggcg | gacaggtatc | cggtaagcgg | cagggtcgga | 7380 |
| acaggagagc | gcacgaggga | gcttccaggg | ggaaacgcct | ggtatcttta | tagtcctgtc | 7440 |
| gggtttcgcc | acctctgact | tgagcgtcga | ttttgtgat | gct | | 7483 |

<210> SEQ ID NO 6  
<211> LENGTH: 6360  
<212> TYPE: DNA  
<213> ORGANISM: Artificial Sequence  
<220> FEATURE:  
<223> OTHER INFORMATION: Vector

<400> SEQUENCE: 6

|  |  |  |  |  |  |  |
|---|---|---|---|---|---|---|
| ctctgacttg | agcgtcgatt | tttgtgatgc | tcgtcagggg | ggcggagcct | atggaaaaac | 60 |
| gccagcaacg | cggccttttt | acggttcctg | gccttttgct | ggccttttgc | tcacatgttc | 120 |
| tttcctgcgt | tatcccctga | ttctgtggat | aaccgtatta | ccgcctttga | gtgagctgat | 180 |
| accgctcgcc | gcagccgaac | gaccgagcgc | agcgagtcag | tgagcgagga | agcggaagag | 240 |
| cgcccaatac | gcaaaccgcc | tctccccgcg | cgttggccga | ttcattaatg | cagctggcac | 300 |
| gacaggtttc | ccgactggaa | agcgggcagt | gagcgcaacg | caattaatgt | gagttacctc | 360 |
| actcattagg | caccccaggc | tttacacttt | atgcttccgg | ctcctatgtt | gtgtggaatt | 420 |
| gtgagcggat | aacaatttca | cacaggaaac | agctatgacc | atgattacgc | caagcgcgca | 480 |
| attaaccctc | actaaaggga | acaaaagctg | gagctcgtag | gaacaatttc | gggcccctgc | 540 |
| gtgttcttct | gaggttcatc | ttttacattt | gcttctgctg | gataattttc | agaggcaaca | 600 |
| aggaaaaatt | agatggcaaa | aagtcgtctt | tcaaggaaaa | atccccacca | tctttcgaga | 660 |
| tccccctgtaa | cttattggca | actgaaagaa | tgaaaggag | gaaaatacaa | aatatactag | 720 |
| aactgaaaaa | aaaaaagtat | aaatagagac | gatatatgcc | aatacttcac | aatgttcgaa | 780 |
| tctattcttc | atttgcagct | attgtaaaat | aataaacat | caagaacaaa | caagctcaac | 840 |
| ttgtcttttc | taagaacaaa | gaataaacac | aaaaacaaaa | agttttttta | attttaatca | 900 |
| aaaagttaac | atgcatcacc | atcaccatca | cactagtgga | tccccgggc | tgcaggaatt | 960 |
| cgatatcaag | cttatcgata | ccgtcgacct | cgagtcatgt | aattagttat | gtcacgctta | 1020 |
| cattcacgcc | ctccccccac | atccgctcta | accgaaaagg | aaggagttag | acaacctgaa | 1080 |
| gtctaggtcc | ctatttattt | ttttatagtt | atgttagtat | taagaacgtt | atttatattt | 1140 |

```
caaattttc ttttttttct gtacagacgc gtgtacgcat gtaacattat actgaaaacc      1200
ttgcttgaga aggttttggg acgctcgaag gctttaattt gcggccggta cccaattcgc      1260
cctatagtga gtcgtattac gcgcgctcac tggccgtcgt tttacaacgt cgtgactggg      1320
aaaaccctgg cgttacccaa cttaatcgcc ttgcagcaca tccccctttc gccagctggc      1380
gtaatagcga agaggcccgc accgatcgcc cttcccaaca gttgcgcagc ctgaatggcg      1440
aatggcgcga cgcgccctgt agcggcgcat taagcgcggc gggtgtggtg gttacgcgca      1500
gcgtgaccgc tacacttgcc agcgccctag cgcccgctcc tttcgctttc ttcccttcct      1560
ttctcgccac gttcgccggc tttccccgtc aagctctaaa tcggggctc ctttagggt       1620 tccgatttag tgctttacgg cacctcgacc ccaaaaaact tgattagggt gatggttcac      1680
gtagtgggcc atcgccctga tagacggttt ttcgcccttt gacgttggag tccacgttct      1740
ttaatagtgg actcttgttc caaactggaa caacactcaa ccctatctcg gtctattctt      1800
ttgatttata agggattttg ccgatttcgg cctattggtt aaaaaatgag ctgatttaac      1860
aaaaatttaa cgcgaatttt aacaaaatat taacgtttac aatttcctga tgcggtattt      1920
tctccttacg catctgtgcg gtatttcaca ccgcataggg taataactga tataattaaa      1980
ttgaagctct aatttgtgag tttagtatac atgcatttac ttataataca gttttttagt      2040
tttgctggcc gcatcttctc aaatatgctt cccagcctgc ttttctgtaa cgttcaccct      2100
ctaccttagc atcccttccc tttgcaaata gtcctcttcc aacaataata atgtcagatc      2160
ctgtagagac cacatcatcc acggttctat actgttgacc caatgcgtct cccttgtcat      2220
ctaaacccac accgggtgtc ataatcaacc aatcgtaacc ttcatctctt ccacccatgt      2280
ctctttgagc aataaagccg ataacaaaat ctttgtcgct cttcgcaatg tcaacagtac      2340
ccttagtata ttctccagta gatagggagc ccttgcatga caattctgct aacatcaaaa      2400
ggcctctagg ttccttttgtt acttcttctg ccgcctgctt caaaccgcta acaatacctg      2460
ggcccaccac accgtgtgca ttcgtaatgt ctgcccattc tgctattctg tatacacccg      2520
cagagtactg caatttgact gtattaccaa tgtcagcaaa ttttctgtct tcgaagagta      2580
aaaaattgta cttggcggat aatgccttta gcggcttaac tgtgccctcc atggaaaaat      2640
cagtcaagat atccacatgt gttttagta aacaaatttt gggacctaat gcttcaacta      2700
actccagtaa ttccttggtg gtacgaacat ccaatgaagc acacaagttt gtttgctttt      2760
cgtgcatgat attaaatagc ttggcagcaa caggactagg atgagtagca gcacgttcct      2820
tatatgtagc tttcgacatg atttatcttc gtttcctgca ggttttttgtt ctgtgcagtt      2880 gggttaagaa tactgggcaa tttcatgttt cttcaacact acatatgcgt atatataccca     2940 atctaagtct gtgctccttc cttcgttctt ccttctgttc ggagattacc gaatcaaaaa      3000
aatttcaaag aaaccgaaat caaaaaaaag aataaaaaaa aatgatgaa ttgaattgaa       3060 aagctgtggt atggtgcact ctcagtacaa tctgctctga tgccgcatag ttaagccagc      3120
cccgacaccc gccaacaccc gctgacgcgc cctgacgggc ttgtctgctc ccggcatccg      3180
cttacagaca agctgtgacc gtctccggga gctgcatgtg tcagaggttt tcaccgtcat      3240
caccgaaacg cgcgagacga agggcctcg tgatacgcct attttatag gttaatgtca       3300 tgataataat ggtttcttag tatgatccaa tatcaaagga aatgatagca ttgaaggatg      3360
agactaatcc aattgaggag tggcagcata tagaacagct aaagggtagt gctgaaggaa      3420
gcatacgata ccccgcatgg aatgggataa tatcacagga ggtactagac tacctttcat      3480
```

```
cctacataaa tagacgcata taagtacgca tttaagcata aacacgcact atgccgttct   3540
tctcatgtat atatatatac aggcaacacg cagatatagg tgcgacgtga acagtgagct   3600
gtatgtgcgc agctcgcgtt gcatttttcgg aagcgctcgt tttcggaaac gctttgaagt   3660
tcctattccg aagttcctat tctctagaaa gtataggaac ttcagagcgc ttttgaaaac   3720
caaaagcgct ctgaagacgc actttcaaaa aaccaaaaac gcaccggact gtaacgagct   3780
actaaaatat tgcgaatacc gcttccacaa acattgctca aaagtatctc tttgctatat   3840
atctctgtgc tatatcccta tataacctac ccatccacct ttcgctcctt gaacttgcat   3900
ctaaactcga cctctacatt ttttatgttt atctctagta ttactcttta gacaaaaaaa   3960
ttgtagtaag aactattcat agagtgaatc gaaaacaata cgaaaatgta aacatttcct   4020
atacgtagta tatagagaca aaatagaaga aaccgttcat aattttctga ccaatgaaga   4080
atcatcaacg ctatcacttt ctgttcacaa agtatgcgca atccacatcg gtatagaata   4140
taatcgggga tgccttattc ttgaaaaaat gcacccgcag cttcgctagt aatcagtaaa   4200
cgcgggaagt ggagtcaggc ttttttatg gaagagaaaa tagacaccaa agtagccttc    4260
ttctaacctt aacggaccta cagtgcaaaa agttatcaag agactgcatt atagagcgca   4320
caaaggagaa aaaagtaat ctaagatgct ttgttagaaa aatagcgctc tcgggatgca    4380
tttttgtaga acaaaaaaga agtatagatt cttgttggt aaaatagcgc tctcgcgttg    4440
catttctgtt ctgtaaaaat gcagctcaga ttctttgttt gaaaaattag cgctctcgcg   4500
ttgcattttt gttttacaaa aatgaagcac agattcttcg ttggtaaaat agcgctttcg   4560
cgttgcattt ctgttctgta aaaatgcagc tcagattctt tgtttgaaaa attagcgctc   4620
tcgcgttgca tttttgttct acaaaatgaa gcacagatgc ttcgttcagg tggcactttt   4680
cggggaaatg tgcgcggaac ccctatttgt ttatttttct aaatacattc aaatatgtat   4740
ccgctcatga gacaataacc ctgataaatg cttcaataat attgaaaaag gaagagtatg   4800
agtattcaac atttccgtgt cgcccttatt cccttttttg cggcattttg ccttcctgtt   4860
tttgctcacc cagaaacgct ggtgaaagta aaagatgctg aagatcagtt gggtgcacga   4920
gtgggttaca tcgaactgga tctcaacagc ggtaagatcc ttgagagttt tcgccccgaa   4980
gaacgttttc caatgatgag cacttttaaa gttctgctat gtggcgcggt attatcccgt   5040
attgacgccg ggcaagagca actcggtcgc cgcatacact attctcagaa tgacttggtt   5100
gagtactcac cagtcacaga aaagcatctt acggatggca tgacagtaag agaattatgc   5160
agtgctgcca taaccatgag tgataacact gcggccaact tacttctgac aacgatcgga   5220
ggaccgaagg agctaaccgc ttttttgcac aacatggggg atcatgtaac tcgccttgat   5280
cgttgggaac cggagctgaa tgaagccata ccaaacgacg agcgtgacac cacgatgcct   5340
gtagcaatgg caacaacgtt gcgcaaacta ttaactggcg aactacttac tctagcttcc   5400
cggcaacaat taatagactg gatggaggcg gataaagttg caggaccact tctgcgctcg   5460
gcccttccgg ctggctggtt tattgctgat aaatctggag ccggtgagcg tgggtctcgc   5520
ggtatcattg cagcactggg gccagatggt aagccctccc gtatcgtagt tatctacacg   5580
acggggagtc aggcaactat ggatgaacga aatagacaga tcgctgagat aggtgcctca   5640
ctgattaagc attggtaact gtcagaccaa gtttactcat atatacttta gattgattta   5700
aaacttcatt tttaatttaa aaggatctag gtgaagatcc ttttgataa tctcatgacc   5760 aaaatccctt aacgtgagtt ttcgttccac tgagcgtcag accccgtaga aaagatcaaa   5820
ggatcttctt gagatccttt ttttctgcgc gtaatctgct gcttgcaaac aaaaaaacca   5880
```

```
ccgctaccag cggtggtttg tttgccggat caagagctac caactctttt tccgaaggta   5940
actggcttca gcagagcgca gataccaaat actgtccttc tagtgtagcc gtagttaggc   6000
caccacttca agaactctgt agcaccgcct acatacctcg ctctgctaat cctgttacca   6060
gtggctgctg ccagtggcga taagtcgtgt cttaccgggt tggactcaag acgatagtta   6120
ccggataagg cgcagcggtc gggctgaacg ggggttcgt gcacacagcc cagcttggag    6180
cgaacgacct acaccgaact gagataccta cagcgtgagc tatgagaaag cgccacgctt   6240
cccgaaggga gaaaggcgga caggtatccg gtaagcggca gggtcggaac aggagagcgc   6300
acgagggagc ttccaggggg aaacgcctgg tatctttata gtcctgtcgg gtttcgccac   6360
```

<210> SEQ ID NO 7
<211> LENGTH: 7590
<212> TYPE: DNA
<213> ORGANISM: Artificial Sequence
<220> FEATURE:
<223> OTHER INFORMATION: Vector

<400> SEQUENCE: 7

```
ctctgacttg agcgtcgatt tttgtgatgc tcgtcagggg ggcggagcct atggaaaaac     60
gccagcaacg cggccttttt acggttcctg ccttttgct ggccttttgc tcacatgttc    120
tttcctgcgt tatcccctga ttctgtggat aaccgtatta ccgcctttga gtgagctgat   180
accgctcgcc gcagccgaac gaccgagcgc agcgagtcag tgagcgagga gcggaagag    240 cgcccaatac gcaaaccgcc tctccccgcg cgttggccga ttcattaatg cagctggcac   300
gacaggtttc ccgactggaa agcgggcagt gagcgcaacg caattaatgt gagttacctc   360
actcattagg caccccaggc tttacacttt atgcttccgg ctcctatgtt gtgtggaatt   420
gtgagcggat aacaatttca cacaggaaac agctatgacc atgattacgc caagcgcgca   480
attaaccctc actaaaggga caaaagctg gagctcgtag gaacaatttc gggcccctgc    540
gtgttcttct gaggttcatc ttttacattt gcttctgctg ataatttttc agaggcaaca   600
aggaaaaatt agatggcaaa aagtcgtctt tcaaggaaaa atccccacca tctttcgaga   660 tccctgtaa cttattggca actgaaagaa tgaaaaggag gaaaatacaa aatatactag   720
aactgaaaaa aaaaagtat aaatagagac gatatatgcc aatacttcac aatgttcgaa    780
tctattcttc atttgcagct attgtaaaat aataaacat caagaacaaa caagctcaac    840 ttgtctttc taagaacaaa gaataaacac aaaaacaaaa agttttttta attttaatca   900
aaaaatggtg gctggaccaa acaaagatct tgaaaacctg gaacgtatga tgtactggaa   960
gaccactttg aaagcttggt catgtttcct tgttggtgct aaattaaacg aaaaattaga   1020
aacagatgat attttaaaag gtatccacaa attattcacg ttgagggttc agttacgttt   1080
gaatgttttc caatatccta aaaaaaggtt tgttaccgaa gagataaatg gttggtctga   1140
tgattttgtt gattttgtcg attatccaac tgatgatttt gatattattg aagcttttaa   1200
acaacaacat aatcaatatt tgaattggg tgttcaaaag cctttatgga aattggttgt    1260
attgaaccat caatatttag ttattctttg tgatcatacc ttatatgatg ggaacactgc   1320
actttatata tgtgaggatt tgatcacaat attgaatgat cgtgatatcc cagttgatag   1380
aattccagat attaaaccat atcatgatct attaaaacca aaacttggac atacaatcaa   1440
aactgtcatc caaactttg caccaaaatg ggcttatcct ttagttaatc tgatttatag   1500
accaaaaagt gaatttgaaa ctggtgcata tgatgattgg ggagtaactc ataaaattga   1560
```

```
aagaacaaca aataaattaa agcacttaat tacaataact aatgaagaat tttccataat   1620
taaaaaatta acaaaatcac atggtgtaaa tttcacagca ttttgggcat atatcaatgt   1680
tcttgcagtt gcacaattgg gaaagtcagc tgttgattta tcaattccat tcaatatgag   1740
aaccaattta ttaccaccag aatatttaag atggtatggt ttattagttt cacatgttac   1800
tttaaatgta cataccaaag ttgatcatga ttcaattgac tgggattttg ttagattttt   1860
aaatggtagt gttgcacata ataccaagt aaaacaatca caaatgcttg gaatgattaa    1920
atatgttagt gctcgtggac ttattgaatc agctttaaaa tcaccaagaa aggtggatt    1980 agaagtttca aacttgggat tgagagtcga tccagatggt gaatcatgga aaaaatatac   2040
ccctgaagaa tttttctttt ctttgccaaa tgatctttca ggttataatg tttcaaatgc   2100
tgtgatttca agtaaaacta aaacaaatat tattttagac ggtgttccag aatttgcaaa   2160
tgaatttcca acgtatgcaa ataacgttga acaattttg agaaatgcaa tcaatgggta    2220
ttatgaataa aattagttat gtcacgctta cattcacgcc ctcccccac atccgctcta    2280 accgaaaagg aaggagttag acaacctgaa gtctaggtcc ctatttattt ttttatagtt   2340
atgttagtat taagaacgtt atttatattt caaatttttc tttttttct gtacagacgc    2400 gtgtacgcat gtaacattat actgaaaacc ttgcttgaga aggtttggg acgctcgaag    2460 gctttaattt gcggccggta cccaattcgc cctatagtga gtcgtattac gcgcgctcac   2520
tggccgtcgt tttacaacgt cgtgactggg aaaaccctgg cgttacccaa cttaatcgcc   2580
ttgcagcaca tccccctttc gccagctggc gtaatagcga gaggcccgc accgatcgcc    2640 cttcccaaca gttgcgcagc ctgaatgcg aatggcgcga cgcgccctgt agcggcgcat    2700
taagcgcggc gggtgtggtg gttacgcgca gcgtgaccgc tacacttgcc agcgccctag   2760
cgcccgctcc tttcgctttc ttcccttcct ttctcgccac gttcgccggc tttccccgtc   2820
aagctctaaa tcggggctc cctttagggt tccgatttag tgctttacgg cacctcgacc    2880
ccaaaaaact tgattagggt gatggttcac gtagtgggcc atcgccctga tagacgttt    2940 ttcgccgttt gacgttggag tccacgttct ttaatagtgg actcttgttc caaactggaa   3000
caacactcaa ccctatctcg gtctattctt ttgatttata agggattttg ccgatttcgg   3060
cctattggtt aaaaaatgag ctgatttaac aaaaatttaa cgcgaatttt aacaaaatat   3120
taacgtttac aatttcctga tgcggtattt tctccttacg catctgtgcg gtatttcaca   3180
ccgcataggg taataactga tataattaaa ttgaagctct aatttgtgag tttagtatac   3240
atgcatttac ttataataca gttttttagt tttgctggcc gcatcttctc aaatatgctt   3300
cccagcctgc ttttctgtaa cgttcaccct ctaccttagc atcccttccc tttgcaaata   3360
gtcctcttcc aacaataata atgtcagatc ctgtagagac cacatcatcc acggttctat   3420
actgttgacc caatgcgtct cccttgtcat ctaaacccac accgggtgtc ataatcaacc   3480
aatcgtaacc ttcatctctt ccacccatgt ctctttgagc aataaagccg ataacaaaat   3540
ctttgtcgct cttcgcaatg tcaacagtac ccttagtata ttctccagta gatagggagc   3600
ccttgcatga caattctgct aacatcaaaa ggcctctagg ttcctttgtt acttcttctg   3660
ccgcctgctt caaaccgcta acaatacctg ggcccaccac accgtgtgca ttcgtaatgt   3720
ctgcccattc tgctattctg tatacacccg cagagtactg caatttgact gtattaccaa   3780
tgtcagcaaa ttttctgtct tcgaagagta aaaaattgta cttggcggat aatgccttta   3840
gcggcttaac tgtgccctcc atggaaaaat cagtcaagat atccacatgt gttttttagta  3900 aacaaatttt gggacctaat gcttcaacta actccagtaa ttccttggtg gtacgaacat   3960
```

```
ccaatgaagc acacaagttt gtttgctttt cgtgcatgat attaaatagc ttggcagcaa    4020
caggactagg atgagtagca gcacgttcct tatatgtagc tttcgacatg atttatcttc    4080
gtttcctgca ggttttgtt ctgtgcagtt gggttaagaa tactgggcaa tttcatgttt    4140
cttcaacact acatatgcgt atatatacca atctaagtct gtgctccttc cttcgttctt    4200
ccttctgttc ggagattacc gaatcaaaaa aatttcaaag aaccgaaat caaaaaaag    4260 aataaaaaaa aaatgatgaa ttgaattgaa agctgtggt atggtgcact ctcagtacaa    4320
tctgctctga tgccgcatag ttaagccagc ccgacaccc gccaacaccc gctgacgcgc    4380
cctgacgggc ttgtctgctc ccggcatccg cttacagaca agctgtgacc gtctccggga    4440
gctgcatgtg tcagaggttt tcaccgtcat caccgaaacg cgcgagacga aagggcctcg    4500
tgatacgcct atttttatag gttaatgtca tgataataat ggtttcttag tatgatccaa    4560
tatcaaagga aatgatagca ttgaaggatg agactaatcc aattgaggag tggcagcata    4620
tagaacagct aaagggtagt gctgaaggaa gcatacgata ccccgcatgg aatgggataa    4680
tatcacagga ggtactagac tacctttcat cctacataaa tagacgcata aagtacgca    4740 tttaagcata aacacgcact atgccgttct tctcatgtat atatatatac aggcaacacg    4800
cagatatagg tgcgacgtga acagtgagct gtatgtgcgc agctcgcgtt gcattttcgg    4860
aagcgctcgt tttcggaaac gctttgaagt tcctattccg aagttcctat tctctagaaa    4920
gtataggaac ttcagagcgc ttttgaaaac caaaagcgct ctgaagacgc actttcaaaa    4980
aaccaaaaac gcaccggact gtaacgagct actaaaatat tgcgaatacc gcttccacaa    5040
acattgctca aaagtatctc tttgctatat atctctgtgc tatatcccta tataacctac    5100
ccatccacct ttcgctcctt gaacttgcat ctaaactcga cctctacatt ttttatgttt    5160
atctctagta ttactcttta gacaaaaaaa ttgtagtaag aactattcat agagtgaatc    5220
gaaaacaata cgaaaatgta aacatttcct atacgtagta tatagagaca aaatagaaga    5280
aaccgttcat aattttctga ccaatgaaga atcatcaacg ctatcacttt ctgttcacaa    5340
agtatgcgca atccacatcg gtatagaata taatcgggga tgcctttatc ttgaaaaaat    5400
gcacccgcag cttcgctagt aatcagtaaa cgcgggaagt ggagtcaggc ttttttatg    5460 gaagagaaaa tagacaccaa agtagccttc ttctaacctt aacggaccta cagtgcaaaa    5520
agttatcaag agactgcatt atagagcgca caaaggagaa aaaagtaat ctaagatgct    5580 ttgttagaaa aatagcgctc tcgggatgca tttttgtaga acaaaaaaga agtatagatt    5640
ctttgttggt aaaatagcgc tctcgcgttg cattctgtt ctgtaaaaat gcagctcaga    5700
ttctttgttt gaaaaattag cgctctcgcg ttgcatttt gttttacaaa aatgaagcac    5760
agattcttcg ttggtaaaat agcgctttcg cgttgcattt ctgttctgta aaatgcagc    5820 tcagattctt tgtttgaaaa attagcgctc tcgcgttgca ttttgttct acaaaatgaa    5880 gcacagatgc ttcgttcagg tggcactttt cgggaaatg tgcgcggaac ccctatttgt    5940
ttatttttct aaatacattc aaatatgtat ccgctcatga gacaataacc ctgataaatg    6000
cttcaataat attgaaaaag gaagagtatg agtattcaac atttccgtgt cgcccttatt    6060
cccttttttg cggcatttg ccttcctgtt ttgctcacc cagaaacgct ggtgaaagta    6120
aaagatgctg aagatcagtt gggtgcacga gtgggttaca tcgaactgga tctcaacagc    6180
ggtaagatcc ttgagagttt tcgccccgaa gaacgttttc caatgatgag cactttaaa    6240 gttctgctat gtggcgcggt attatcccgt attgacgccg ggcaagagca actcggtcgc    6300
```

```
cgcatacact attctcagaa tgacttggtt gagtactcac cagtcacaga aaagcatctt    6360
acggatggca tgacagtaag agaattatgc agtgctgcca taaccatgag tgataacact    6420
gcggccaact tacttctgac aacgatcgga ggaccgaagg agctaaccgc ttttttgcac    6480
aacatggggg atcatgtaac tcgccttgat cgttgggaac cggagctgaa tgaagccata    6540
ccaaacgacg agcgtgacac cacgatgcct gtagcaatgg caacaacgtt gcgcaaacta    6600
ttaactggcg aactacttac tctagcttcc cggcaacaat taatagactg gatgaggcg    6660 gataaagttg caggaccact tctgcgctcg gcccttccgg ctggctggtt tattgctgat    6720
aaatctggag ccggtgagcg tgggtctcgc ggtatcattg cagcactggg gccagatggt    6780
aagccctccc gtatcgtagt tatctacacg acggggagtc aggcaactat ggatgaacga    6840
aatagacaga tcgctgagat aggtgcctca ctgattaagc attggtaact gtcagaccaa    6900
gtttactcat atatacttta gattgattta aaacttcatt tttaatttaa aaggatctag    6960
gtgaagatcc tttttgataa tctcatgacc aaaatccctt aacgtgagtt ttcgttccac    7020
tgagcgtcag accccgtaga aaagatcaaa ggatcttctt gagatccttt ttttctgcgc    7080
gtaatctgct gcttgcaaac aaaaaaacca ccgctaccag cggtggtttg tttgccggat    7140
caagagctac caactctttt tccgaaggta actggcttca gcagagcgca gataccaaat    7200
actgtccttc tagtgtagcc gtagttaggc caccacttca agaactctgt agcaccgcct    7260
acatacctcg ctctgctaat cctgttacca gtggctgctg ccagtggcga taagtcgtgt    7320
cttaccgggt tggactcaag acgatagtta ccggataagg cgcagcggtc gggctgaacg    7380
gggggttcgt gcacacagcc cagcttggag cgaacgacct acaccgaact gagatcccta    7440
cagcgtgagc tatgagaaag cgccacgctt cccgaaggga gaaaggcgga caggtatccg    7500
gtaagcggca gggtcggaac aggagagcgc acgagggagc ttccaggggg aaacgcctgg    7560
tatctttata gtcctgtcgg gtttcgccac                                    7590

<210> SEQ ID NO 8
<211> LENGTH: 8933
<212> TYPE: DNA
<213> ORGANISM: Artificial Sequence
<220> FEATURE:
<223> OTHER INFORMATION: Vector

<400> SEQUENCE: 8
cgtcaggggg gcggagccta tggaaaaacg ccagcaacgc ggccttttta cggttcctgg      60
ccttttgctg gccttttgct cacatgttct ttcctgcgtt atcccctgat tctgtggata     120
accgtattac cgcctttgag tgagctgata ccgctcgccg cagccgaacg accgagcgca     180
gcgagtcagt gagcgaggaa gcggaagagc gcccaatacg caaaccgcct ctccccgcgc     240
gttggccgat tcattaatgc agctggcacg acaggtttcc cgactggaaa gcgggcagtg     300
agcgcaacgc aattaatgtg agttacctca ctcattaggc accccaggct ttacacttta     360
tgcttccggc tcctatgttg tgtggaattg tgagcggata acaatttcac acaggaaaca     420
gctatgacca tgattacgcc aagcgcgcaa ttaaccctca ctaaagggaa caaaagctgg     480
agctcgtagg aacaatttcg ggcccctgcg tgttcttctg aggttcatct tttacatttg     540
cttctgctgg ataattttca gaggcaacaa ggaaaaatta gatggcaaaa agtcgtcttt     600
caaggaaaaa tccccaccat ctttcgagat cccctgtaac ttattggcaa ctgaaagaat     660 gaaaggagg aaaatacaaa atatactaga actgaaaaaa aaaagtata aatagagacg     720 atatatgcca atacttcaca atgttcgaat ctattcttca tttgcagcta ttgtaaaata     780
```

```
ataaaacatc aagaacaaac aagctcaact tgtcttttct aagaacaaag aataaacaca      840
aaaacaaaaa gttttttttaa ttttaatcaa aaagtgaata tattttttca agggcccata      900
tatatatata aacacaagaa atgtttattt gaatcattac aatttacttt cttaacctca      960
tcatcaaata tgtcatttaa atatatcaat caaaatgatt caaaatcatt atcaaattta     1020
aaatataaat tatcaaaaaa tcatgcaaga caaatgggtt tttagaaga ttttttttgca     1080 attttacaac gtcaaaaaat gtataaatca tttttcgtta tgtgtaaata taatgaaaaa     1140
attgatgatt ttaaaatttt attccattca ttaagattat taatattaaa attcccaata     1200
ttagcttcca caataattac tcaaaatgtt ccaattaata taaaacctcg tccttatgat     1260
tatattcaaa ttattgatga aataaaattt aatgatttgg tttgggattt aagacctgaa     1320
tattcaaatt tattacaaga agattttatta aataaattaa atgatttaat tataccatat     1380
gaagataata aattagtttg gagattagga atcttggatg attatacatt aattttttata    1440 acaaatcatg ttttacatga tggaatatct ggtaaaaata ttttttaatga attatcatta    1500 attttttaatc aattggactt ggattcttta agtgatgatg atgatatcgt gttcaattat    1560
tcacaagatc atttgaattt aggtgaatta ccaaaaccta taactgatct tatgaatcat    1620
attccatcaa ttaaatcttt accaagatat atttataatt cattaattga accaaaactt    1680
ttttgttcat caactttaat tcaaggtcat cttaagaata ttcattatag agttaatata    1740
aatccaatgg aattattaaa aattaaatca ttattatcaa aaaatagttt caataatgtt    1800
aaattaactt taacaccttt cattcaatct atttggaatt atactttata tcaagatgaa    1860
tattataaat catcaaaatc tttattaggt attgcagtgg attctcgtca atttattaat    1920
aaagatgaac aagatttata taaatttggt ttaaatgtat caggttttag taaaatttcc    1980
aaaccaatga aattaattac atggaataaa attaatcaaa ttaatcaaga tttaaaaatt    2040
tcattaaaat tgaaaaaacc tttatattca atgggtatat taggttggga taaaatgatt    2100
aaaaataaac atttagatgt tgatttacca aaaattatga ataaaagaac aggttcaact    2160
ttttcaaata ttggtataat cctaaataac agtgaatcaa atgataaatt tcaaattatt    2220
gatgcaatgt ttacacaaca ttttaatgtt cattttatg atttctcaat cactgcaatt    2280
tctacaatga ctggtgggtt aaatattata attacatcac cagaatctat tggaattgaa    2340
aatttagaaa gaatttgtaa aaaatttcat gaaaatttag ttttatgtga tattaaataa    2400
ggataatttg ggcccgatga attagttatg tcacgcttac attcacgccc tcccccaca     2460 tccgctctaa ccgaaaagga aggagttaga caacctgaag tctaggtccc tatttatttt    2520
tttatagtta tgttagtatt aagaacgtta tttatatttc aaatttttct tttttttctg    2580
tacagacgcg tgtacgcatg taacattata ctgaaaacct tgcttgagaa ggttttggga    2640
cgctcgaagg cttttaatttg cggccggtac ccaattcgcc ctatagtgag tcgtattacg    2700
cgcgctcact ggccgtcgtt ttacaacgtc gtgactggga aaaccctggc gttacccaac    2760
ttaatcgcct tgcagcacat ccccctttcg ccagctggcg taatagcgaa gaggcccgca    2820
ccgatcgccc ttcccaacag ttgcgcagcc tgaatggcga atggcgcgac gcgcctgta    2880 gcggcgcatt aagcgcggcg ggtgtggtgg ttacgcgcag cgtgaccgct acacttgcca    2940
gcgccctagc gcccgctcct ttcgctttct tcccttcctt tctcgccacg ttcgccggct    3000
ttccccgtca agctctaaat cggggctctc ctttagggtt ccgatttagt gctttacggc    3060
acctcgaccc caaaaaactt gattagggtg atggttcacg tagtgggcca tcgccctgat    3120
```

```
agacggtttt tcgcccttt g acgttggagt ccacgttctt taatagtgga ctcttgttcc   3180
aaactggaac aacactcaac cctatctcgg tctattcttt tgatttataa gggattttgc   3240
cgatttcggc ctattggtta aaaatgagc tgatttaaca aaatttaac gcgaatttta    3300 acaaaatatt aacgtttaca atttcctgat gcggtatttt ctccttacgc atctgtgcgg   3360
tatttcacac cgcatatcga cggtcgagga gaacttctag tatatccaca tacctaatat   3420
tattgcctta ttaaaaatgg aatcccaaca attacatcaa aatccacatt ctcttcaaaa   3480
tcaattgtcc tgtacttcct tgttcatgtg tgttcaaaaa cgttatattt ataggataat   3540
tatactctat ttctcaacaa gtaattggtt gtttggccga gcggtctaag gcgcctgatt   3600
caagaaatat cttgaccgca gttaactgtg ggaatactca ggtatcgtaa gatgcaagag   3660
ttcgaatctc ttagcaacca ttattttttt cctcaacata acgagaacac acaggggcgc   3720
tatcgcacag aatcaaattc gatgactgga aattttttgt taatttcaga ggtcgcctga   3780
cgcatatacc ttttcaact gaaaaattgg gagaaaaagg aaaggtgaga ggccggaacc   3840
ggcttttcat atagaataga gaagcgttca tgactaaatg cttgcatcac aatacttgaa   3900
gttgacaata ttatttaagg acctattgtt ttttccaata ggtggttagc aatcgtctta   3960 cttttctaact tttcttacct tttacatttc agcaatatat atatatattt caaggatata   4020
ccattctaat gtctgcccct atgtctgccc ctaagaagat cgtcgttttg ccaggtgacc   4080
acgttggtca agaaatcaca gccgaagcca ttaaggttct taaagctatt tctgatgttc   4140
gttccaatgt caagttcgat ttcgaaaatc atttaattgg tggtgctgct atcgatgcta   4200
caggtgtccc acttccagat gaggcgctgg aagcctccaa gaaggttgat gccgttttgt   4260
taggtgctgt ggctggtcct aaatggggta ccggtagtgt tagacctgaa caaggtttac   4320
taaaaatccg taaagaactt caattgtacg ccaacttaag accatgtaac tttgcatccg   4380
actctctttt agacttatct ccaatcaagc cacaatttgc taaaggtact gacttcgttg   4440
ttgtcagaga attagtggga ggtatttact ttggtaagag aaaggaagac gatggtgatg   4500
gtgtcgcttg ggatagtgaa caatacaccg ttccagaagt gcaagaatc acaagaatgg   4560 ccgctttcat ggcccctacaa catgagccac cattgcctat ttggtccttg gataaagcta   4620
atcttttggc ctcttcaaga ttatggagaa aaactgtgga ggaaaccatc aagaacgaat   4680
tccctacatt gaaggttcaa catcaattga ttgattctgc cgccatgatc ctagttaaga   4740
acccaaccca cctaaatggt attataatca ccagcaacat gtttggtgat atcatctccg   4800
atgaagcctc cgttatccca ggttcctgg gtttgttgcc atctgcgtcc ttggcctctt   4860
tgccagacaa gaacaccgca tttggttttgt acgaaccatg ccacggttct gctccagatt   4920
tgccaaagaa taaggttgac cctatcgcca ctatcttgtc tgctgcaatg atgttgaaat   4980
tgtcattgaa cttgcctgaa gaaggtaagg ccattgaaga tgcagttaaa aaggttttgg   5040
atgcaggtat cagaactggt gatttaggtg gttccaacag taccaccgaa gtcggtgatg   5100
ctgtcgccga agaagttaag aaaatccttg cttaaaaaga ttctcttttt ttatgatatt   5160
tgtacataaa ctttataaat gaaattcata atagaaacga cacgaaatta caaaatggaa   5220
tatgttcata gggtagacga aactatatac gcaatctaca tacatttatc aagaaggaga   5280
aaaaggagga tagtaaagga atacaggtaa gcaaattgat actaatggct caacgtgata   5340
aggaaaaaga attgcacttt aacattaata ttgacaagga ggagggcacc acacaaaaag   5400
ttaggtgtaa cagaaaatca tgaaactacg attcctaatt tgatattgga ggattttctc   5460
taaaaaaaaa aaaatacaac aaataaaaaa cactcaatga cctgaccatt tgatggagtt   5520
```

-continued

```
taagtcaata ccttcttgaa gcatttccca taatggtgaa agttccctca agaattttac    5580
tctgtcagaa acggccttac gacgtagtcg atatggtgca ctctcagtac aatctgctct    5640
gatgccgcat agttaagcca gccccgacac ccgccaacac ccgctgacgc gccctgacgg    5700
gcttgtctgc tcccggcatc cgcttacaga caagctgtga ccgtctccgg gagctgcatg    5760
tgtcagaggt tttcaccgtc atcaccgaaa cgcgcgagac gaaagggcct cgtgatacgc    5820
ctattttat aggttaatgt catgataata atggtttctt agtatgatcc aatatcaaag     5880
gaaatgatag cattgaagga tgagactaat ccaattgagg agtggcagca tatagaacag    5940
ctaaagggta gtgctgaagg aagcatacga taccccgcat ggaatgggat aatatcacag    6000
gaggtactag actacctttc atcctacata aatagacgca tataagtacg catttaagca    6060
taaacacgca ctatgccgtt cttctcatgt atatatatat acaggcaaca cgcagatata    6120
ggtgcgacgt gaacagtgag ctgtatgtgc gcagctcgcg ttgcatttc ggaagcgctc     6180
gttttcggaa acgctttgaa gttcctattc cgaagttcct attctctaga aagtatagga    6240
acttcagagc gcttttgaaa accaaaagcg ctctgaagac gcactttcaa aaaccaaaa    6300
acgcaccgga ctgtaacgag ctactaaaat attgcgaata ccgcttccac aaacattgct    6360
caaaagtatc tctttgctat atatctctgt gctatatccc tataaccct acccatccac     6420
ctttcgctcc ttgaacttgc atctaaactc gacctctaca tttttatgt ttatctctag     6480
tattactctt tagacaaaaa aattgtagta agaactattc atagagtgaa tcgaaaacaa    6540
tacgaaaatg taaacatttc ctatacgtag tatatagaga caaaatagaa gaaaccgttc    6600
ataatttct gaccaatgaa gaatcatcaa cgctatcact ttctgttcac aaagtatgcg    6660
caatccacat cggtatagaa tataatcggg gatgccttta tcttgaaaaa atgcaccccgc  6720
agcttcgcta gtaatcagta aacgcgggaa gtggagtcag gcttttttta tggaagagaa    6780
aatagacacc aaagtagcct tcttctaacc ttaacggacc tacagtgcaa aaagttatca    6840
agagactgca ttatagagcg cacaaaggag aaaaaaagta atctaagatg ctttgttaga    6900
aaaatagcgc tctcgggatg cattttttgta gaacaaaaaa gaagtataga ttctttgttg    6960
gtaaaatagc gctctcgcgt tgcatttctg ttctgtaaaa atgcagctca gattctttgt    7020
ttgaaaaatt agcgctctcg cgttgcattt ttgttttaca aaaatgaagc acagattctt    7080
cgttggtaaa atagcgcttt cgcgttgcat ttctgttctg taaaaatgca gctcagattc    7140
tttgtttgaa aaattagcgc tctcgcgttg cattttgtt ctacaaaatg aagcacagat     7200
gcttcgttca ggtggcactt ttcggggaaa tgtgcgcgga accctatt gtttattttt      7260
ctaaatacat tcaaatatgt atccgctcat gagacaataa ccctgataaa tgcttcaata    7320
atattgaaaa aggaagagta tgagtattca acatttccgt gtcgcccta ttccctttttt   7380
tgcggcattt tgccttcctg ttttgctca cccagaaacg ctggtgaaag taaaagatgc     7440
tgaagatcag ttgggtgcac gagtgggtta catcgaactg gatctcaaca gcggtaagat    7500
ccttgagagt tttcgccccg aagaacgttt tccaatgatg agcactttta agttctgct    7560
atgtggcgcg gtattatccc gtattgacgc cgggcaagag caactcggtc gccgcataca    7620
ctattctcag aatgacttgg ttgagtactc accagtcaca gaaaagcatc ttacggatgg    7680
catgacagta agagaattat gcagtgctgc cataaccatg agtgataaca ctgcggccaa    7740
cttacttctg acaacgatcg gaggaccgaa ggagctaacc gcttttttgc acaacatggg    7800
ggatcatgta actcgccttg atcgttggga accggagctg aatgaagcca taccaaacga    7860
```

-continued

```
cgagcgtgac accacgatgc ctgtagcaat ggcaacaacg ttgcgcaaac tattaactgg      7920
cgaactactt actctagctt cccggcaaca attaatagac tggatggagg cggataaagt      7980
tgcaggacca cttctgcgct cggcccttcc ggctggctgg tttattgctg ataaatctgg      8040
agccggtgag cgtgggtctc gcggtatcat tgcagcactg gggccagatg gtaagccctc      8100
ccgtatcgta gttatctaca cgacggggag tcaggcaact atggatgaac gaaatagaca      8160
gatcgctgag ataggtgcct cactgattaa gcattggtaa ctgtcagacc aagtttactc      8220
atatatactt tagattgatt taaaacttca ttttttaattt aaaaggatct aggtgaagat      8280
cctttttgat aatctcatga ccaaaatccc ttaacgtgag ttttcgttcc actgagcgtc      8340
agaccccgta gaaaagatca aaggatcttc ttgagatcct ttttttctgc gcgtaatctg      8400
ctgcttgcaa acaaaaaaac caccgctacc agcggtggtt tgtttgccgg atcaagagct      8460
accaactctt tttccgaagg taactggctt cagcagagcg cagataccaa atactgtcct      8520
tctagtgtag ccgtagttag gccaccactt caagaactct gtagcaccgc ctacatacct      8580
cgctctgcta atcctgttac cagtggctgc tgccagtggc gataagtcgt gtcttaccgg      8640
gttggactca agacgatagt taccggataa ggcgcagcgg tcgggctgaa cggggggttc      8700
gtgcacacag cccagcttgg agcgaacgac ctacaccgaa ctgagatacc tacagcgtga      8760
gctatgagaa agcgccacgc ttcccgaagg gagaaaggcg acaggtatc cggtaagcgg       8820 cagggtcgga acaggagagc gcacgaggga gcttccaggg ggaaacgcct ggtatcttta      8880
tagtcctgtc gggtttcgcc acctctgact tgagcgtcga ttttttgtgat gct            8933
```

```
<210> SEQ ID NO 9
<211> LENGTH: 57
<212> TYPE: DNA
<213> ORGANISM: Artificial Sequence
<220> FEATURE:
<223> OTHER INFORMATION: Primer

<400> SEQUENCE: 9
aaaacaaaaa gttttttttaa ttttaatcaa aaagtgaata tatttttttca agggccc       57

<210> SEQ ID NO 10
<211> LENGTH: 52
<212> TYPE: DNA
<213> ORGANISM: Artificial Sequence
<220> FEATURE:
<223> OTHER INFORMATION: Primer

<400> SEQUENCE: 10
gagggcgtga atgtaagcgt gacataacta attcatcggg cccaaattat cc              52

<210> SEQ ID NO 11
<211> LENGTH: 51
<212> TYPE: DNA
<213> ORGANISM: Artificial Sequence
<220> FEATURE:
<223> OTHER INFORMATION: Primer

<400> SEQUENCE: 11
aaaacaaaaa gttttttttaa ttttaatcaa aaaatggtgg ctggaccaaa c              51

<210> SEQ ID NO 12
<211> LENGTH: 59
<212> TYPE: DNA
```

```
<213> ORGANISM: Artificial Sequence
<220> FEATURE:
<223> OTHER INFORMATION: Primer

<400> SEQUENCE: 12
gggagggcgt gaatgtaagc gtgacataac taattttatt cataataccc attgattgc        59
```

ACETYLTRANSFERASE FROM WICKERHAMOMYCES CIFERRII

CROSS-REFERENCE TO RELATED APPLICATIONS

This application is a §371 national phase of PCT International Application No. PCT/EP2013/055092, filed Mar. 13, 2013, which claims the benefit of German Application No. DE102012007491, filed on Apr. 11, 2012, the contents of each of which are herein incorporated by reference in their entireties.

FIELD OF INVENTION

Novel enzymes which provide acetylated sphingoid bases are the subject of the invention.

INCORPORATION BY REFERENCE OF SEQUENCE LISTING

The Sequence Listing in an ASCII text file, named 31307_Sequence_Listing.txt of 61 KB, created on Oct. 8, 2014, and submitted to the United States Patent and Trademark Office via EFS-Web, is incorporated herein by reference.

PRIOR ART

*Pichia ciferrii* has already been used since the start of the 60s for the production of sphingoid bases and sphingolipids. The yields of sphingoid bases and sphingolipids from wild type strains are always open to improvement.

Sphingoid bases, in particular phytosphingosine, sphingosine and sphinganine, are used in diverse ways as cosmetic active substances for protection and care of the skin.

They are incorporated into cosmetic care products either directly or after chemical conversion to skin-identical ceramides.

The non-conventional yeast *Pichia ciferrii* is characterized in that it secretes relatively large quantities of acetylated sphingoid bases, mainly tetraacetylphytosphingosine (TAPS) and triacetylsphinganine (TriASa), into the culture medium. The TAPS formed can be extracted from the culture broth by extraction and is subsequently chemically converted into free phytosphingosine, and into various ceramides.

An efficient acetylation is the basic requirement for the transport of the sphingoid bases into the culture medium: enzymatic tests with microsome fractions have shown that those strains with high productivity of acetylated sphingoid bases (high producers) display a markedly increased specific acetyltransferase activity compared to the low producers (Barenholz et al., 1971; Barenhoz et al., 1973). Hence this enzymatic activity could be identified as one of the main reasons for the efficient production of acetylated sphingoid bases by various *Pichia ciferrii* strains.

All attempts at purification, characterization and identification of such enzymes have hitherto failed, so that neither the proteins, nor the corresponding genes are known.

The purpose of the invention was to provide enzymes and coding sequences thereof which are capable of acetylating sphingoid bases.

DESCRIPTION OF INVENTION

Surprisingly it has been found that the enzymes described below are capable of solving the problem posed for the invention.

Isolated nucleic acids coding for acetyltransferases as described in the claims are therefore a subject of the present invention.

Recombinant cells which exhibit modified activity of the enzymes according to the invention are a further subject of the invention.

The acetyltransferases described with the present invention and the DNA sequences encoding them offer a number of advantages. They can be used for acetylating defined substrates (sphingoid bases) biotechnologically and highly specifically on various functional groups (hydroxy and amino groups). Compared to a chemical acetylation process, fewer side products are generated thereby, as a result of which the losses in yield and laborious purification steps can be minimized. The invention thus has great potential, especially for applications which require high product purity. Particularly high product purities are necessary inter alia in the cosmetics, food and luxury consumables and pharmaceuticals sectors, so that here the invention has particularly great potential. The biotechnological production of acetylated sphingoid bases can be effected with the present invention essentially in two different ways: firstly, the production can be effected via the biocatalysis approach, wherein selected sphingoid bases are enzymatically acetylated in a suitable reactor with addition of the acetyltransferase(s). Secondly, the genes of the acetyltransferases can be used to generate recombinant microbial strains by genetic engineering methods (Metabolic Engineering), which are capable of directly synthesizing acetylated sphingoid bases from simple C and N sources in a fermentative process. In comparison to a chemical process, the fermentative process is less expensive and ecologically more sustainable. Moreover, it is stereospecific, which is not ensured in a chemical total synthesis.

By use of only one of the acetyltransferases described in this invention, or the genes thereof, incompletely acetylated sphingoid bases can be specifically created. These can have particular biological effects and can thus be used for particular applications, e.g. as cosmetic or pharmaceutical active substances or precursors thereof.

Incompletely acetylated sphingoid bases can only be chemically prepared extremely laboriously, hence a considerable cost advantage arises for the biotechnological approach.

Unless otherwise stated, all percentages (%) stated are mass percent.

A contribution to the solution of the problem is provided by an isolated nucleic acid, which has a sequence selected from the groups [A1 to G1]

A1) a sequence according to Seq ID No. 1, wherein this sequence codes for a protein which is capable of converting phytosphingosine to triacetylphytosphingosine by transfer of the acetyl residues from three molecules of acetyl coenzyme A, B1) an intron-free sequence which is derived from a sequence according to A1) and which encodes the same protein or peptide as the sequence according to Seq ID No. 1, C1) a sequence which encodes a protein or peptide which includes the amino acid sequence according to Seq ID No. 2 and which is capable of converting phytosphingosine to triacetylphytosphingosine by transfer of the acetyl residues from three molecules of acetyl coenzyme A, D1) a sequence which is at least 70%, particularly preferably at least 90%, still more preferably at least 95% and most preferably at least 99% identical with a sequence according to one of the groups A1) to C1), particularly preferably according to group A1), wherein this sequence codes for a protein or peptide which is capable of converting phytosphingosine to triacetylphytosphingosine by transfer of the acetyl residues from three molecules of acetyl coenzyme A, E1) a sequence which hybridizes or would hybridize taking account of the degeneracy of the genetic code with the complementary strand of a sequence according to one of the groups A1) to D1), particularly preferably according to group A1), wherein this sequence codes for a protein or peptide which is capable of converting phytosphingosine to triacetylphytosphingosine by transfer of the acetyl residues from three molecules of acetyl coenzyme A, F1) a derivative of a sequence according to one of the groups A1) to E1), particularly preferably according to group A1) obtained by substitution, addition, inversion and/or deletion of at least one base, preferably of at least 2 bases, still more preferably of at least 5 bases and most preferably at least 10 bases but preferably of not more than 100 bases, particularly preferably of not more than 50 bases and most preferably of not more than 25 bases, wherein this derivative codes for a protein or peptide which is capable of converting phytosphingosine to triacetylphytosphingosine by transfer of the acetyl residues from three molecules of acetyl coenzyme A, G1) a complementary sequence to a sequence according to one of the groups A1) to F1), particularly preferably according to group A1).

A further contribution to the solution of the problem is provided by an isolated nucleic acid which has a sequence selected from the groups [A2 to G2]

A2) a sequence according to Seq ID No. 3, wherein this sequence codes for a protein which is capable of converting triacetylphytosphingosine to tetraacetylphytosphingosine by transfer of the acetyl residue from one molecule of acetyl coenzyme A, B2) an intron-free sequence which is derived from a sequence according to A2) and which encodes the same protein or peptide as the sequence according to Seq ID No. 3, C2) a sequence which encodes a protein or peptide which includes the amino acid sequence according to Seq ID No. 4, and which is capable of converting triacetylphytosphingosine to tetraacetylphytosphingosine by transfer of the acetyl residue from one molecule of acetyl coenzyme A, D2) a sequence which is at least 70%, particularly preferably at least 90%, still more preferably at least 95% and most preferably at least 99% identical with a sequence according to one of the groups A2) to C2), particularly preferably according to group A2), wherein this sequence codes for a protein or peptide which is capable of converting triacetylphytosphingosine to tetraacetylphytosphingosine by transfer of the acetyl residue from one molecule of acetyl coenzyme A, E2) a sequence which hybridizes or would hybridize taking account of the degeneracy of the genetic code with the complementary strand of a sequence according to one of the groups A2) to D2), particularly preferably according to group A2), wherein this sequence codes for a protein or peptide which is capable of converting triacetylphytosphingosine to tetraacetylphytosphingosine by transfer of the acetyl residue from one molecule of acetyl coenzyme A, F2) a derivative of a sequence according to one of the groups A2) to E2), particularly preferably according to group A2), obtained by substitution, addition, inversion and/or deletion of at least one base, preferably of at least 2 bases, still more preferably of at least 5 bases and most preferably at least 10 bases but preferably of not more than 100 bases, particularly preferably of not more than 50 bases and most preferably of not more than 25 bases, wherein this derivative codes for a protein or peptide which is capable of converting triacetylphytosphingosine to tetraacetylphytosphingosine by transfer of the acetyl residue from one molecule of acetyl coenzyme A, G2) a complementary sequence to a sequence according to one of the groups A2) to F2), particularly preferably according to group A2), The "nucleotide identity" or "amino acid identity" is determined here by means of known methods. Special computer programs with algorithms taking account of specific requirements are generally used.

Preferred methods for the determination of identity firstly generate the greatest match between the sequences to be compared. Computer programs for the determination of identity include, but are not limited to, the GCG program package, including GAP (Deveroy, J. et al., Nucleic Acid Research 12 (1984), page 387, Genetics Computer Group University of Wisconsin, Medicine (Wi), and BLASTP, BLASTN and FASTA (Altschul, S. et al., Journal of Molecular Biology 215 (1990), pages 403-410. The BLAST program can be obtained from the National Center For Biotechnology Information (NCBI) and from other sources (BLAST Handbuch, Altschul S. et al., NCBI NLM NIH Bethesda ND 22894; Altschul S. et al., above).

The well-known Smith-Waterman algorithm can also be used for the determination of nucleotide identity.

Preferred parameters for the determination of "nucleotide identity" with use of the BLASTN program (Altschul, S. et al., Journal of Molecular Biology 215 (1990), pages 403-410, are:

| | |
|---|---|
| Expect Threshold: | 10 |
| Word size: | 28 |
| Match Score: | 1 |
| Mismatch Score: | −2 |
| Gap costs: | Linear |

The above parameters are the default parameters in the nucleotide sequence comparison.

The GAP program is also suitable for use with the above parameters.

Preferred parameters for the determination of "amino acid identity" with use of the BLASTP program (Altschul, S. et al., Journal of Molecular Biology 215 (1990), pages 403-410, are:

| | |
|---|---|
| Expect Threshold: | 10 |
| Word size: | 3 |
| Matrix: | BLOSUM62 |
| Gap costs: | Existence: 11; Extension: 1 |
| Compositional adjustments: | Conditional compositional score matrix adjustment |

The above parameters are the default parameters in the amino acid sequence comparison.

The GAP program is also suitable for use with the above parameters.

In connection with the present invention, an identity of 60% according to the above algorithm means 60% identity. The same applies for higher identities.

The characteristic "sequence which hybridizes or would hybridize taking account of the degeneracy of the genetic code with the complementary strand of a sequence" designates a sequence which under preferably stringent conditions hybridizes or would hybridize taking account of the degeneracy of the genetic code with the complementary strand of a reference sequence. For example, the hybridizations can be performed at 68° C. in 2×SSC or according to the protocol of the digoxigenin-labeling kit from Boehringer (Mannheim). Preferred hybridization conditions are for example incubation at 65° C. overnight in 7% SDS, 1% BSA, 1 mM EDTA and 250 mM sodium phosphate buffer (pH 7.2) followed by washing at 65° C. with 2×SSC; 0.1% SDS.

The derivatives of the DNA isolated according to the invention which according to alternatives F1) or F2) can be obtained by substitution, addition, inversion and/or deletion of one or more bases of a sequence according to one of the groups A1) to E1) and A2) to E2) in particular include those sequences which in the protein which they encode lead to conservative amino acid replacements such as for example the replacement of glycine by alanine or of aspartic acid by glutamic acid. Such function-neutral mutations are described as sense mutations and lead to no fundamental change in the activity of the polypeptide. Furthermore, it is known that changes at the N and/or C terminus of a polypeptide do not significantly affect its function or can even stabilize this, so that correspondingly DNA sequences, in which bases are attached at the 3' end or at the 5' end of the sequence with the nucleic acids according to the invention are also encompassed by the present invention. Those skilled in the art find information on this inter alia in Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in well-known genetics and molecular biology textbooks.

The nucleic acid according to the invention is preferably a vector, in particular an expression vector or a gene overexpression cassette. Possible vectors are all vectors known to those skilled in the art which are usually used for the introduction of DNA into a host cell. These vectors can replicate either autonomously since they possess replication origins, such as for example that of the 2μ plasmid or ARS (autonomously replicating sequences), or integrate into the chromosomes (non-replicating plasmids). Vectors are also understood to mean linear DNA fragments which possess no replication origins whatever, such as for example gene insertion or gene overexpression cassettes. Gene overexpression cassettes usually consist of a marker, the genes to be overexpressed and regulatory regions relevant for the expression of the genes, such as for example promoters and terminators. Optionally, gene overexpression cassettes can also include specific DNA sequences which via homologous recombination mechanisms enable targeted integration into the host genome. Depending on the structure of the gene overexpression cassettes, these can preferably be integrated into the host genome in single or multiple form.

Preferred vectors are selected from the group comprising plasmids and cassettes, such as for example *E. coli*-yeast shuttle plasmids, and expression vectors, gene insertion or gene overexpression cassettes are particularly preferable.

A contribution to the solution of the initially stated problem is provided by the cells described below, which can advantageously be used for the production of acetylated sphingoid bases, in particular acetylated phyosphingosine. The cells according to the invention can for example be contacted in a biotransformation with exogenously prepared sphingoid base, which the cells then acetylate by means of their enzyme equipment, or else cells which themselves already produce the sphingoid bases to be acetylated are used as starting strains for the production of the cells according to the invention.

Hence a subject of the present invention is a cell, preferably an isolated cell, characterized in that it has been genetically modified such that compared to the wild type thereof it has modified activity of at least one of the enzymes $E_1$ and/or $E_2$, wherein the enzyme $E_1$ is selected from an enzyme $E_1$ with the polypeptide sequence Seq ID No. 2 or with a polypeptide sequence in which up to 25%, preferably up to 20%, particularly preferably up to 15%, in particular up to 10, 9, 8, 7, 6, 5, 4, 3, 2 or 1% of the amino acid residues are modified compared to the reference sequence Seq ID No. 2 by deletion, insertion, substitution or a combination thereof and which still possesses at least 10%, preferably 50%, particularly preferably 80%, in particular more than 90% of the enzymatic activity of the enzyme with the reference sequence Seq ID No. 2, wherein enzymatic activity for an enzyme $E_1$ is understood to mean the ability to convert phytosphingosine to triacetylphytosphingosine by transfer of the acetyl residues from three molecules of acetyl coenzyme A, and the enzyme $E_2$ is selected from an enzyme $E_2$ with the polypeptide sequence Seq ID No. 4 or with a polypeptide sequence in which up to 25%, preferably up to 20%, particularly preferably up to 15%, in particular up to 10, 9, 8, 7, 6, 5, 4, 3, 2 or 1% of the amino acid residues are modified compared to the reference sequence Seq ID No. 4 by deletion, insertion, substitution or a combination thereof and which still possesses at least 10%, preferably 50%, particularly preferably 80%, in particular more than 90% of the enzymatic activity of the enzyme with the reference sequence Seq ID No. 4, wherein enzymatic activity for an enzyme $E_2$ is understood to mean the ability to convert triacetylphytosphingosine to tetraacetylphytosphingosine by transfer of the acetyl residue from one molecule of acetyl coenzyme A.

Herein, "wild type" designates a cell the genome whereof is present in a state which has arisen naturally through evolution. The term is used both for the whole cell and also for individual genes. Hence the term "wild type" in particular does not include those cells or those genes whose gene sequences have been at least partly modified by man by recombinant methods.

Preferably the modified activity is an increased activity. The term "increased activity of an enzyme" should preferably be understood as increased intracellular activity.

It is obvious to those skilled in the art that with regard to the term "modified (increased or decreased) activity compared to the wild type thereof", cells or cell populations which are in identical, or comparable, states for example as regards growth phase, culture age and culturing phase, are compared.

The explanations that now follow on the increasing of the enzyme activity in cells apply both for the increasing of the activity of the enzyme $E_1$ to $E_2$ and also for all enzymes mentioned below, whose activity can if necessary be increased.

Essentially, an increase in the enzymatic activity can be achieved by increasing the copy number of the gene sequence or the gene sequences which code for the enzyme, using a strong promoter or an improved ribosome binding site, weakening a negative regulation of gene expression, for example with transcription regulators, or strengthening a positive regulation of gene expression, for example with transcription regulators, modifying the codon utilization of the gene, increasing the half-life of the mRNA or the enzyme in various ways, modifying the regulation of the expression of the gene or using a gene or allele which codes for a corresponding enzyme with increased activity and optionally combining these measures. Cells genetically modified according to the invention are for example created by transformation, transduction, conjugation or a combination of these methods with a vector which contains the desired gene, an allele of this gene or parts thereof and optionally a promoter enabling the expression of the gene. Heterologous expression in particular is achieved by integration of the gene or the allele into the chromosome of the cell or into an extrachromosomally replicating vector.

An overview of the possibilities for increasing the enzyme activity in cells in the case of pyruvate carboxylase is given in DE-A-100 31 999, which is herewith introduced as a reference and the disclosure content whereof regarding the possibilities for increasing enzyme activity in cells forms a part of the disclosure of the present invention.

The expression of the above-mentioned and all below-mentioned enzymes and genes is detectable in gel by means of 1- and 2-dimensional protein gel separation followed by optical identification of the protein concentration with appropriate evaluation software. When the increasing of an enzyme activity is exclusively based on increasing the expression of the corresponding gene, then the quantification of the increase in the enzyme activity can be simply determined by comparison of the 1- or 2-dimensional protein separations between wild type and genetically modified cell. A common method for preparation of the protein gels in the case of coryneform bacteria and for identification of the proteins is the procedure described by Hermann et al. (Electrophoresis, 22: 1712.23 (2001)). The protein concentration can also be analyzed by Western blot hybridization with an antibody specific for the protein to be detected (Sambrook et al., Molecular Cloning: a laboratory manual, 2nd Ed. Cold Spring Harbor Laboratory Press, Cold Spring Harbor, N.Y. USA, 1989) followed by optical evaluation with appropriate software for concentration determination (Lohaus and Meyer (1989) Biospektrum, 5: 32-39; Lottspeich (1999) Angewandte Chemie 111: 2630-2647). The activity of DNA-binding proteins can be measured by DNA band shift assays (also described as gel retardation) (Wilson et al. (2001) Journal of Bacteriology, 183: 2151-2155). The effect of DNA-binding proteins on the expression of other genes can be detected by various well-described methods of the reporter gene assay (Sambrook et al., Molecular Cloning: a laboratory manual, 2nd Ed. Cold Spring Harbor Laboratory Press, Cold Spring Harbor, N.Y. USA, 1989). Intracellular enzymatic activities can be determined by various described methods (Donahue et al. (2000) Journal of Bacteriology 182 (19): 5624-5627; Ray et al. (2000) Journal of Bacteriology 182 (8):2277-2284; Freedberg et al. (1973) Journal of Bacteriology 115 (3): 816-823). If no specific methods for the determination of the activity of a certain enzyme are stated in the following explanations, the determination of the increase in the enzyme activity and also the determination of the reduction of an enzyme activity is preferably performed by the methods described in Hermann et al., Electophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the increasing of the enzyme activity is effected by mutation of the endogenous gene, then such mutations can be created either undirectedly by classical methods, such as for example by UV irradiation or by mutagenic chemicals, or specifically by genetic engineering methods such as deletion(s), insertion(s) and/or nucleotide substitution(s). Through these mutations, modified cells are obtained. Particularly preferable mutants of enzymes are in particular also those enzymes which are no longer or at least less feedback-, product- or substrate-inhibitable compared to the wild type enzyme.

If the increasing of the enzyme activity is effected by increasing the synthesis of an enzyme, then for example the copy number of the relevant gene is increased or the promoter and regulation region or the ribosome binding site which is located upstream of the structural gene is mutated. Expression cassettes which are incorporated upstream of the structural gene have a similar effect. Additionally, by means of inducible promoters it is possible to increase expression at any desired time. Further, however, so-called "enhancers" can also be assigned to the enzyme gene as regulatory sequences, which likewise cause increased gene expression via improved interaction between RNA polymerase and DNA. Expression is also improved by measures to prolong the lifetime of the mRNA. Moreover, enzyme activity is also intensified by prevention of the degradation of the enzyme protein. Here, the genes or gene constructs are present either in plasmids of different copy number or are integrated in the chromosome and if necessary amplified. Alternatively, moreover, overexpression of the relevant genes can be achieved by modification of the medium composition and culturing. Those skilled in the art find directions for this inter alia in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP-A-0 472 869, in U.S. Pat. No. 4,601,893, in Schwarzer and Puhler (Bio/Technology 9, 84-87 (1991), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Gene 134, 15-24 (1993)), in JP-A-10-229891, in Jensen and Hammer (Biotechnology and Bioengineering 58, 191-195 (1998)) and in well-known genetics and molecular biology textbooks. The measures described above, like the mutations, also result in genetically modified cells.

To increase the expression of the particular genes, for example episomal or integrative plasmids are used. In principle, as plasmids or vectors, all embodiments available to those skilled in the art for this purpose are possible. Such plasmids and vectors can for example be inferred from the brochures of Novagen, Promega, New England Biolabs, Clontech or Gibco BRL. Further preferable plasmids and vectors can be found in: Glover, D. M. (1985) DNA cloning: a practical approach, Vol. I-III, IRL Press Ltd., Oxford; Rodriguez, R. L. and Denhardt, D. T (eds) (1988) Vectors: a survey of molecular cloning vectors and their uses, 179-204, Butterworth, Stoneham; Goeddel, D. V. (1990) Systems for heterologous gene expression, Methods Enzymol. 185, 3-7; and Sambrook, J.; Fritsch, E. F. and Maniatis, T. (1989), Molecular cloning: a laboratory manual, 2nd ed., Cold Spring Harbor Laboratory Press, New York.

The plasmid vector which contains the gene to be amplified is then transferred into the desired strain by conjugation or transformation. The method of conjugation is for example described in Schäfer et al., Applied and Environmental Microbiology 60: 756-759 (1994). Methods for transformation are for example described in Schorsch et al., Current Genetics 55(4): 381-389 (2009), Thierbach et al., Applied Microbiology and Biotechnology 29: 356-362 (1988), Dunican and Shivnan, Bio/Technology 7: 1067-1070 (1989) and Tauch et al., FEMS Microbiology Letters 123: 343-347 (1994). In the case of integrative plasmids or linear gene overexpression cassettes, these are integrated into the genome of the host strain either ectopically (not homologously) or specifically by homologous recombination mechanisms ("crossing over"). Depending on the exact structure of the plasmid or of the gene overexpression cassette and on the particular recombination event, the resulting strain contains one or several copies of the gene concerned.

The wording "an increased activity of an enzyme $E_x$ compared to the wild type thereof" used above and in the explanations below should preferably always be understood to mean an activity of the particular enzyme $E_x$ increased by a factor of at least 2, particularly preferably of at least 10, still more preferably of at least 100, still more preferably yet of at least 1,000 and most preferably of at least 10,000. Furthermore, the cell according to the invention which has "an increased activity of an enzyme $E_x$ compared to the wild type thereof", in particular also includes a cell, the wild type whereof has no or at least no detectable activity of this enzyme $E_x$, and which only displays detectable activity of this enzyme $E_x$ after increasing of the enzyme activity, for example by overexpression. In this connection, the term "overexpression" or the wording "increasing of expression" used in the explanations below also includes the case that a starting cell, for example a wild type cell, displays no or at least no detectable expression and detectable synthesis of the enzyme $E_x$ is only induced by recombinant procedures.

Changes of amino acid residues of a given polypeptide sequence which lead to no significant changes in the properties and function of the given polypeptide are well-known to those skilled in the art. Thus for example so-called conserved amino acids can be exchanged for one another; examples of such suitable amino acid substitutions are: Ala by Ser; Arg by Lys; Asn by Gln or His; Asp by Glu; Cys by Ser; Gln by Asn; Glu by Asp; Gly by Pro; His by Asn or Gln; Ile by Leu or Val; Leu by Met or Val; Lys by Arg or Gln or Glu; Met by Leu or Ile; Phe by Met or Leu or Tyr; Ser by Thr; Thr by Ser; Trp by Tyr; Tyr by Trp or Phe; and Val by Ile or Leu. Likewise, it is known that changes, particularly at the N or C terminus of a polypeptide for example in the form of amino acid insertions or deletions often exert no significant influence on the function of the polypeptide.

The activity of the enzyme $E_1$ is determined as described in Barenholz and Gatt, The Journal of Biological Chemistry 247 (21): 6827-6833 (1972), wherein phytosphingosine is used as substrate and the acetylation thereof compared to a reference system identical except for the property "containing as enzyme $E_1$ an enzyme with Seq ID No. 2" is measured.

The activity of the enzyme $E_2$ is determined as described in Barenholz and Gatt, The Journal of Biological Chemistry 247 (21): 6827-6833 (1972), wherein triacetylated phytosphingosine is used as substrate and the acetylation thereof compared to a reference system identical except for the property "containing as enzyme $E_2$ an enzyme with Seq ID No. 4" is measured.

Cells preferred according to the invention exhibit intensified activity of both enzymes $E_1$ and $E_2$.

In one preferable alternative of the invention, for the production of triacetyl phytosphingosine and the diacetylated sphingoid bases diacetyl sphingosine, diacetyl sphinganine, diacetyl-6-hydroxysphingosine and diacetyl sphingadienine, cells which have decreased activity of the enzyme $E_2$ compared to the wild type thereof are useful. In this connection, cells which as well as the decreased activity of the enzyme $E_2$ have increased activity of the enzyme $E_1$ are in particular useful.

Cells preferred according to the invention are microorganisms, in particular yeasts or bacteria, wherein preferable yeast cells in particular are selected from the genera *Saccharomyces, Pichia, Yarrowia, Kluyveromyces, Hansenula, Ashbya* and *Candida*, with the species *Saccharomyces cerevisiae, Kluyveromyces lactis, Hansenula polymorpha, Pichia pastoris, Pichia ciferrii, Yarrowia lipolytica, Candida albicans, Candida utilis* and *Ashbya gossypii* being particularly preferable.

It is particularly preferable according to the invention if for the production of the cells according to the invention starting strains are used which already have a high sphingoid bases titer; hence cells preferable according to the invention are in particular derived from the cells described in WO2006048458, WO2007131720 and DE102011110959.9 and from strains selected from the group consisting of *Pichia ciferrii* NRRL Y-1031 F-60-10 (Wickerham and Stodola, Journal of Bacteriology 80: 484-491 (1960), the *Pichia ciferrii* strains disclosed in the examples of WO 95/12683 and the strain *Pichia ciferri* CS.PCΔPro2, described in Schorsch et al., 2009, Curr Genet. 55, 381-9.

A further contribution to the solution of the problem posed for the invention is provided by the use of the cells according to the invention for the production of sphingoid bases and/or sphingolipids.

In connection with the present invention, the term "sphingoid bases" should be understood to mean phytosphingosine, sphingosine, sphingadienine, 6-hydroxysphingosine and sphinganine (dihydrosphingosine), also in the acetylated form, such as for example tetraacetylphytosphingosine, triacetylphytosphingosine, diacetylphytosphingosine, O-acetylphytosphingosine, triacetylsphinganine, diacetylsphinganine, O-acetylsphinganine, triacetylsphingosine, diacetylsphingosine, O-acetylsphingosine, tetraacetyl-6-hydroxysphingosine, triacetyl-6-hydroxysphingosine, diacetyl-6-hydroxysphingosine, O-acetyl-6-hydroxysphingosine, triacetyl-sphingadienine, diacetylsphingadienine and O-acetylsphingadienine.

In connection with the present invention, the term "sphingolipids" should be understood to mean compounds which comprise sphingoid bases covalently linked with a fatty acid via an amide bond. The fatty acid can be saturated or singly or multiply unsaturated.

The length of the fatty acid side-chain can vary. The fatty acid side-chain can further possess functional groups such as hydroxy groups. The sphingolipids include for example phytoceramides, ceramides and dihydroceramides, and the more complex glucosylceramides (cerebrosides) and the inositol phosphorylceramides, mannosyl-inositol phosphorylceramides and mannosyl di-inositol phosphorylceramides. Also included here among the sphingolipids are sphingoid bases linked with an acetyl residue via an amide bond, such as for example N-acetylphytosphingosine, N-acetylsphinganine, N-acetylsphingosine, N-acetyl-6-hydroxysphingosine and N-acetylsphingadienine. These compounds are also known under the name short-chain ceramides.

In particular the use of the cells according to the invention for the production of sphingoid bases and/or sphingolipids selected from the group, phytosphingosine, sphingosine, 6-hydroxysphingosine, sphinganine (dihydrosphingosine), tetraacetyl-phytosphingosine (TAPS), triacetylphytosphingosine, diacetylphytosphingosine, O-acetylphytosphingosine, N-acetylphytosphingosine, triacetylsphinganine (TriASa), diacetylsphinganine, O-acetylsphinganine, N-acetylsphinganine, triacetylsphingosine (TriASo), diacetylsphingosine, O-acetylsphingosine, N-acetylsphingosine, tetraacetyl-6-hydroxysphingosine, triacetyl-6- hydroxysphingosine, diacetyl-6-hydroxysphingosine, O-acetyl-6-hydroxysphingosine, N-acetyl-6-hydroxysphingosine, triacetylsphingadienine, diacetylsphingadienine, O-acetylsphingadienine and N-acetylsphingadienine is advantageous. Quite especially preferable is the use of the cells according to the invention for the production of tetraacetylphytosphingosine (TAPS).

One preferable use according to the invention is characterized according to the invention in that cells preferable according to the invention as described above are used.

A further contribution to the solution of the problem posed for the invention is provided by a method for the production of sphingoid bases and/or sphingolipids comprising the process steps a) contacting the cell according to the invention with a medium containing a carbon source,
b) culturing the cell under conditions which enable the cell to form sphingoid bases and/or sphingolipids from the carbon source and
c) optionally isolation of the sphingoid bases and/or sphingolipids formed.

Methods preferred according to the invention use cells mentioned above as preferred according to the invention.

As the carbon source, carbohydrates such as for example glucose, fructose, glycerin, saccharose, maltose and molasses, but also alcohols such as for example ethanol organic acids such as for example acetate are used. As the nitrogen source, for example ammonia, ammonium sulfate, ammonium nitrate, ammonium chloride, organic nitrogen compounds (such as yeast extract, malt extract, peptone, and corn steep liquor) can be used. Furthermore, inorganic compounds such as for example phosphate, magnesium, potassium, zinc and iron salts and others can be used. Suitable culturing conditions which enable the cell to form sphingoid bases and/or sphingolipids from the carbon source are known to those skilled in the art for *Pichia ciferri* for example from WO2006048458 and WO2007131720. Those skilled in the art can without the need for experiment apply these conditions to other cell types.

The process according to the invention is particularly suitable for the production of tetraacetylphytosphingosine (TAPS), in particular when cells which exhibit intensified activity of both enzymes $E_1$ and $E_2$ are used.

The enzymes described can also advantageously be used for acetylation of the amino groups of aliphatic primary amines with 6 to 18 C atoms such as for example hexadecylamine.

Thus a further subject of the present invention is a method for the production of N-acetylated, primary aliphatic amines comprising the process steps A) contacting at least one of the enzymes $E_1$ or $E_2$, where the enzyme $E_1$ is selected from an enzyme $E_1$ with the polypeptide sequence Seq ID No. 2 or with a polypeptide sequence in which up to 25%, preferably up to 20%, particularly preferably up to 15%, in particular up to 10, 9, 8, 7, 6, 5, 4, 3, 2 or 1% of the amino acid residues are modified compared to the reference sequence Seq ID No. 2 by deletion, insertion, substitution or a combination thereof and which still possesses at least 10%, preferably 50%, particularly preferably 80%, in particular more than 90% of the enzymatic activity of the enzyme with the reference sequence Seq ID No. 2, wherein enzymatic activity for an enzyme $E_1$ is understood to mean the ability to convert phytosphingosine to triacetylphytosphingosine by transfer of the acetyl residues from three molecules of acetyl coenzyme A, and the enzyme $E_2$ is selected from an enzyme $E_2$ with the polypeptide sequence Seq ID No. 4 or with a polypeptide sequence in which up to 25%, preferably up to 20%, particularly preferably up to 15%, in particular up to 10, 9, 8, 7, 6, 5, 4, 3, 2 or 1% of the amino acid residues are modified compared to the reference sequence Seq ID No. 4 by deletion, insertion, substitution or a combination thereof and which still possesses at least 10%, preferably 50%, particularly preferably 80%, in particular more than 90% of the enzymatic activity of the enzyme with the reference sequence Seq ID No. 4, wherein enzymatic activity for an enzyme $E_2$ is understood to mean the ability to convert triacetylphytosphingosine to tetraacetylphytosphingosine by transfer of the acetyl residue from one molecule of acetyl coenzyme A, with a medium containing a primary, aliphatic amine, in particular selected from those which have 6 to 18 carbon atoms, which are preferably linear, and Acetyl-CoA, and B) optionally isolation of the acetylated amines formed.

Methods preferred according to the invention preferably use as enzymes $E_1$ and/or $E_2$ isolated and/or recombinantly produced enzymes and/or cells mentioned above as according to the invention.

In the examples presented below, the present invention is described by way of example, without it being intended that the invention, the range of application whereof emerges from the whole description and the claims, be restricted to the embodiments mentioned in the examples.

EXAMPLES

Overexpression of PcSLI1 in the Yeast *Saccharomyces cerevisiae* Strain K26

For the overexpression of PcSLI1 in *Saccharomyces cerevisiae* strain K26, the PcSLI1-ORF was firstly cloned into the 2μ vector p426HXT7-6HIS (Hamacher et al. Microbiology 148: 2783-2788 (2002), (Seq ID No. 6)). For this, the PcSLI1-ORF was amplified by polymerase chain reaction (PCR). Firstly, genomic DNA was isolated from *P. ciferrii* by a modified cethyltrimethylammonium bromide (CTAB) method (Murray and Thompson; Nucleic Acids Res 8, 4321-4325 (1980)). For this, cells of a culture grown in YEPD liquid medium (1% w/v yeast extract, 1% w/v peptone, 2% w/v glucose) (≥2 ml, $OD_{600nm}$>1) were harvested, resuspended in 400 μl CTAB buffer [2% (w/v) CTAB, 100 mM Tris-HCl (pH 8.0), 20 mM EDTA, 1.4 M NaCl], treated with 200 μl of glass beads (0.25-0.5 mm Ø) and disintegrated for 8 mins at 4° C. on a "Vibrax VXR basic" (2200 rpm). Next, the preparation was incubated for 30 mins at 65° C. After addition of one volume of chloroform followed by homogenization for 10 secs, the preparation was centrifuged for 5 mins at 16,000 g. The DNA-containing supernatant was removed and the DNA precipitated for at least 30 mins at −20° C. with 0.7 volumes of isopropanol. Then, after centrifugation for 15 mins at 16,000 g and 4° C., the sediment was washed with 70% ice-cold ethanol, dried and resuspended in 50 μl $H_2O$.

The PCR amplification of the PcSLI1-ORF was then effected with genomic *P. ciferrii* DNA as template and with the two oligonucleotides SLI1.HXT7.fw (Seq ID No. 11) and SLI1.CYC1.ry (Seq ID No. 12). The primers used here each possessed at the 5' end regions which were homologous with the integration region in the target vector. In *S. cerevisiae*, these homologous ends enable a homologous recombination between a linearized vector and PCR fragments in order to create a circularized plasmid which can be proliferated in vivo. As the DNA polymerase, the Phusion™ High-Fidelity DNA polymerase (Finnzymes) was used according to the manufacturer's directions. For the amplification, the following temperature profile was selected: step 1: 98° C., 2 mins (denaturation); step 2: 98° C., 15 secs (denaturation); step 3: 60° C., 25 secs (annealing); step 4: 72° C., 80 secs (elongation); step 5: 72° C., 5 min (elongation). Steps 2-4 were repeated 35×. After agarose gel electrophoresis, the resulting 1.4 kb PCR fragment was purified using the "NucleoSpin® Extract II" gel extraction kit (Macherey-Nagel) according to the manufacturer's instructions.

The plasmid p426HXT7-6HIS (Seq ID No. 6) was digested with BamHI/EcoRI according to the manufacturer's instructions. After agarose gel electrophoresis, the resulting 6.3 kb vector fragment was also purified using the "NucleoSpin® Extract II" gel extraction kit (Macherey-Nagel) according to the manufacturer's instructions.

The cloning of the PCR-amplified PcSLI1-ORF into the BamHI/EcoRI-cleaved vector was effected by in vivo recombination in S. cerevisiae. The basic method is described in Oldenburg et al. (Nucleic Acids Res 25: 451-452 (1994)). The two purified DNA fragments were transformed together into S. cerevisiae CEN.PK113-13D (K26), during which the protocol of Gietz and Schiestl (Nat Protoc 2: 31-34 (2007)) was followed. The cells were then plated out onto synthetic minimal medium (0.16% w/v yeast nitrogen base, 0.5% w/v ammonium sulfate, 2% w/v glucose, 2% w/v agar). Transformants could thereby be selected which on the basis of homologous recombination of the DNA fragment with the linearized vector possessed a stable, circularized plasmid. Plasmids were then isolated from the yeast clones. For this, cells of a 2 ml culture grown in synthetic minimal medium ($OD_{600nm}$>1) were harvested, washed and resuspended in 400 µl buffer 1 [50 mM glucose; 10 mM EDTA (Titriplex III); 25 mM Tris-HCl (pH 8); RNase A (100 µg/ml)]. After addition of 400 µl buffer 2 (0.2 M NaOH; 1% SDS) and careful mixing, ca. ⅔ of the volume of glass beads (0.25-0.5 mm ⌀) were added and the cells disintegrated at 4° C. for 8 mins on a "Vibrax VXR basic" at 2200 rpm. 500 µl of supernatant were mixed with 250 µl buffer 3 [5 M potassium acetate (pH 5.5)], incubated for 10 mins on ice and centrifuged for 5 mins at 16,000 g. The supernatant was precipitated for at least 30 mins at −20° C. with isopropanol in the ratio 1:1 and then centrifuged for 20 mins at 16,000 g. The pelleted DNA was washed with 70% ethanol (−20° C.) and dissolved in 50 µl water. Next, the plasmid DNA was transformed into E. coli by electroporation as per Dower et al. (Nucleic Acids Res 16: 6127-6145 (1988)). For the electroporation, the Gene Pulser® was used under the following conditions: voltage: 2-2.5 kV; resistance: 200Ω; capacitance: 25 µF. Transformants were selected on solid LB medium (1% w/v tryptone, 0.5% w/v yeast extract, 0.5% w/v NaCl, 2% Agar, pH 7.5) supplemented with 40 µg/ml ampicillin. For the isolation of the plasmids from E. coli, the clones were grown on a shaker overnight at 37° C. in 5 ml of liquid LB medium supplemented with 40 µg/ml ampicillin, then the GeneJET™ plasmid Miniprep Kit (Fermentas GmbH) was used according to the manufacturer's instructions.

The plasmids were then characterized by restriction analysis and sequencing. The correct integration of the PcSLI1-ORF into the linearized vector yielded the 7.6 kb plasmid pCS.426.SLI1 (Seq ID No. 7), in which the PcSLI1-ORF is under the control of the shortened $HXT7^{392-1}$ promoter fragment and the CYC1 terminator from S. cerevisiae. This arrangement enables a constitutive overexpression of PcSLI1 in S. cerevisiae.

The plasmids pCS.426.SLI1 (Seq ID No. 7) and the control plasmid p426HXT7-6HIS (Seq ID No. 6) were then transformed into S. cerevisiae strain K26, for which the method of Gietz and Schiestl (Nat Protoc 2: 31-34 (2007)) was again followed. Transformants were once again selected on synthetic minimal medium (0.16% w/v yeast nitrogen base, 0.5% w/v ammonium sulfate, 2% w/v glucose, 2% w/v agar). Next, the transformants were cultured in liquid TAPS medium [composition per liter: 33 g glucose monohydrate, 20 g potassium hydrogen phthalate, 4.83 g ammonium chloride, 1 g yeast extract, 1 g potassium dihydrogen phosphate, 0.88 g magnesium sulfate heptahydrate, 0.2 g calcium chloride dihydrate, 60 mg sodium chloride, 59 mg myoinositol, trace elements [37.3 mg ammonium-iron(II) sulfate hexahydrate, 7.5 mg copper(II) sulfate pentahydrate, 5 mg zinc sulfate heptahydrate, 1.5 mg potassium iodide, 0.6 mg manganese (II) sulfate monohydrate, 0.6 mg boric acid, 0.6 mg sodium molybdate dihydrate] and vitamins (3 mg nicotinic acid, 3 mg calcium D-pantothenate, 3 mg thiamine, 2 mg 4-aminobenzoic acid, 0.3 mg pyridoxine, 10 µg biotin); pH 5.4], in order to investigate the effect of the overexpression of PcSLI1 on the production of acetylated sphingoid bases. The transformants were grown aerobically at 30° C. on a rotary shaking device at 200-250 rpm. The cells were firstly grown in 5 ml TAPS as a preculture and on attainment of the stationary growth phase were used for the inoculation of 20 ml TAPS medium (≙ main culture).

Main cultures were started with an $OD_{600}$ nm of 0.1. For the analysis of acetylated sphingoid bases by LC-MS/MS, on attainment of the stationary phase 1 ml samples of the culture broth were withdrawn and stored at −20° C. until further processing. The extraction of the lipids was effected by the method of Bjerve et al. (Anal. Biochem. 58: 238-245 (1974)). For this, 20 µl of culture broth were taken up in ten times the volume of n-butanol. 20 ng of odd number C17 phytosphingosine, C17 sphinganine and deuterium-labeled $d_9$ triacetyl-sphinganine were added as internal standards and the sample was vigorously mixed at 70° C. Next, the sample was centrifuged at 1000×g for 5 mins, and 10 µl of the supernatant were withdrawn and diluted tenfold in 50/50% (v/v) methanol/$H_2O$.

For the LC-MS/MS analysis of the sphingolipids, a Thermo Accela HPLC (Thermo Fisher Scientific Inc., Waltham, Mass., USA) unit was used. The injected sample volume was 5 µl. The column used was a reversed phase Hypersil Gold C18 column, thermostatted at 40° C. (1.9 µm particles; 50×2.1 mm; #25002-052130; Thermo Fisher Scientific Inc., Waltham, Mass., USA) and protected by a Microbore Guard column (Nucleodur C18 ISIS; 3 µm particles; 5×1 mm; #717759; Macherey-Nagel, Dueren, Germany). The mobile phase had a flow rate of 200 µl/min and consisted of (A) $H_2O$ with 0.1% v/v formic acid and 2% v/v acetonitrile, and (B) acetonitrile with 0.1% v/v formic acid. After 1 min initially with 70% B, a 4-step gradient was used for the elution: 1) increase from 70% B to 94% over 1.5 min; 2) increase from 94% B to 100% over 3.5 mins; 3) maintenance of 100% B over 3.5 mins; 4) reduction from 100% B to 70% and maintenance for 2.5 mins. The MS/MS analysis was performed as Multiple Reaction Monitoring (MRM) in the positive ionization mode. Applied mass transitions and collision energies are shown in table 1.

TABLE 1

Mass transitions and collision energies. IS, Internal standard (deuterated or sphingolipid with odd number chain length). Bold printed values were used as qualifiers.

|  | Precursor ion (m/z) | Product ion(s) (m/z) | Collision energy (eV) |
|---|---|---|---|
| Sphinganine | 302.3 | 284.4/266.4 | 10/25 |
| C17-Sphinganine IS | 288.3 | 270.4/252.4 | 10/25 |
| Phytosphingosine | 318.3 | 300.4/286.4 | 11/25 |
| C17-Phytosphingosine IS | 304.3 | 286.4/250.4 | 11/25 |
| Triacetylsphinganine | 428.3 | 368.4/266.4 | 10/25 |
| Triacetylphytosphingosine | 444.3 | 384.4/264.4 | 10/25 |
| Tetraacetylphytosphingosine | 486.3 | 426.4/264.4 | 10/25 |
| $d_9$-Triacetylsphinganine IS | 437.3 | 374.4/266.4 | 10/25 |

Instrument settings were as follows: capillary voltage, 3.5 kV; capillary temperature, 350° C., declustering voltage, 10 V; sheath gas pressure, 5 au (arbitrary units); ion sweep gas pressure, 0 au; auxiliary gas pressure, 5 au, S-lens RF amplitude, 50 V; collision energy, 10-35 eV; argon collision gas pressure, 1.0 mTorr; cycle length, 600 msecs; resolution of quadrupole 1 and 3 was 0.70 (fwhm). The Xcalibur software version 2.1 (Thermo Fisher Scientific Inc., Waltham, Mass., USA) was used for data recording and analysis.

The effect of PcSLI1 expression on the production of acetylated sphingoid bases in *S. cerevisiae* is shown in table 2. Markedly increased titers were mainly to be recorded in the case of diacetylsphinganine, triacetylsphinganine and triacetylphytosphingosine, while the quantity of tetraacetylphytosphingosine formed was unchanged in comparison to the control strain. This is a clear indication that the PcSLI1 protein can only transfer three acetyl residues onto phytosphingosine or sphinganine. This protein cannot however catalyze the final acetylation of triacetylphytosphingosine onwards to tetraacetylphytosphingosine.

TABLE 2

Production of acetylated and free sphingoid bases in recombinant *S. cerevisiae* strains. K26L, strain *S. cerevisiae* K26 transformed with the control plasmid p426HXT7-6HIS; K26SLI1, strain *S. cerevisiae* K26 transformed with the PcSLI1 overexpression plasmid pCS.426.SLI1; Sa, sphinganine; DiASa, diacetylsphinganine; TriASa, triacetylsphinganine; Ps, phytosphingosine; TriAPS, triacetylphytosphingosine; TAPS, tetraacetylphytosphingosine; the values show the titers in mg/l determined in the fermentation broth.

|  | Sa | DiASa | TriASa | Ps | TriAPS | TAPS |
|---|---|---|---|---|---|---|
| K26L | 0.65 | 0 | 0.1 | 1.0 | 0 | 0.1 |
| K26SLI1 | 0.4 | 1.5 | 0.7 | 0.6 | 1.4 | 0.1 |

Overexpression of PcSLI1 and PcATF1 in the Strain *Saccharomyces cerevisiae* Strain K26

For complete acetylation of phytosphingosine to tetraacetylphytosphingosine in *Saccharomyces cerevisiae* strain K26 the simultaneous overexpression of PcSLI1 and PcATF1 was required. For the overexpression of PcSLI1, the plasmid pCS.426.SLI1, the construction whereof was described in the previous example, is used. The expression vector p426HXT7-6HIS (Seq ID No. 6) used for this carries the *S. cerevisiae* URA3 marker gene. For the overexpression of PcATF1, the PcATF1-ORF must firstly be cloned into a suitable expression vector which carries an alternative marker gene. For this, the plasmid p425HXT7-6HIS (Becker and Boles; Appl Environ Microbiol 69: 4144-4150 (2003), (Seq ID No. 5)), which carries the *S. cerevisiae* LEU2 gene as selection marker, is used.

Firstly, the PcATF1-ORF including 19 by of the PcATF1 terminator is amplified from genomic *P. ciferrii* DNA by PCR. As primers, the oligonucleotides ATF2-HXT.fw (Seq ID No. 9) and ATF2-CYC.ry (Seq ID No. 10) are used. The primers used for this each possess at the 5' end regions which are homologous to the integration region in the target vector. In *S. cerevisiae*, these homologous ends enable homologous recombination between a linearized vector and PCR fragments in order to create a circularized plasmid which can be proliferated in vivo.

As the DNA polymerase, the Phusion™ High-Fidelity DNA polymerase (Finnzymes) is used according to the manufacturer's instructions. For the amplification, the following temperature profile is selected: step 1: 98° C., 2 mins (denaturation); step 2: 98° C., 15 secs (denaturation); step 3: 61° C., 25 secs (annealing); step 4: 72° C., 80 secs (elongation); step 5: 72° C., 5 mins (elongation). Steps 2-4 are repeated 35×. After SDS gel electrophoresis, the resulting 1.6 kb PCR fragment is purified using the "NucleoSpin® Extract II" gel extraction kit (Macherey-Nagel) according to the manufacturer's instructions.

The plasmid p425HXT7-6HIS (Seq ID No. 5) is digested with BamHI/HindIII according to the manufacturer's instructions. The resulting 7.5 kb vector fragment is also purified with the "NucleoSpin® Extract II" gel extraction kit (Macherey-Nagel) according to the manufacturer's instructions after SDS gel electrophoresis.

The cloning of the PCR-amplified PcATF1-ORF into the BamHI/EcoRI-cleaved vector is effected by in vivo recombination into *S. cerevisiae*. The basic method is described in Oldenburg et al. (Nucleic Acids Res 25: 451-452 (1994)). The two purified DNA fragments are transformed together into *S. cerevisiae* strain 10480-2C (Mösch and Fink, Genetics 145: 671-684 (1997)), for which the protocol of Gietz and Schiestl (Nat Protoc 2: 31-34 (2007)) is followed. The cells are then plated out onto minimal medium (0.16% w/v yeast nitrogen base, 0.5% w/v ammonium sulfate, 2% w/v glucose, 2% w/v agar) supplemented with 20 mg/l uracil. Thereby, transformants can be selected which because of homologous recombination of the DNA fragment with the linearized vector possess a stable, circularized plasmid. Plasmids are then isolated from the yeast clones. For this, cells from a 2 ml culture grown in synthetic minimal medium supplemented with 20 mg/l L-histidine HCl, 20 mg/l uracil and 20 mg/l L-tryptophan ($OD_{600nm}$>1) are harvested, washed and resuspended in 400 µl buffer 1 [50 mM glucose; 10 mM EDTA (Titriplex III); 25 mM Tris HCl (pH 8); RNase A (100 µg/ml)]. After addition of 400 µl buffer 2 (0.2 M NaOH; 1% SDS) and careful mixing, ca. % of the volume of glass beads (0.25-0.5 mm ○) are added and the cells disintegrated at 4° C. for 8 mins on a "Vibrax VXR basic" at 2200 rpm. 500 µl of supernatant are mixed with 250 µl buffer 3 [5 M potassium acetate (pH 5.5)], incubated for 10 mins on ice and centrifuged for 5 mins at 16,000 g. The supernatant is precipitated for at least 30 mins at −20° C. with isopropanol in the ratio 1:1 and then centrifuged for 20 mins at 16,000 g. The pelleted DNA is washed with 70% ethanol (−20° C.) and dissolved in 50 µl water. Next, the plasmid DNA is transformed into E. coli by electroporation according to Dower et al. (Nucleic Acids Res 16: 6127-6145 (1988)). For the electroporation, the Gene Pulser® is used under the following conditions: voltage: 2-2.5 kV; resistance: 200Ω; capacitance: 25 µF. Transformants are selected on solid LB medium (1% w/v tryptone, 0.5% w/v yeast extract, 0.5% w/v NaCl, 2% agar, pH 7.5) supplemented with 40 µg/ml ampicillin. For the isolation of the plasmids from E. coli, the clones are grown in 5 ml liquid LB medium supplemented with 40 µg/ml ampicillin overnight at 37° C. on a shaker, then the GeneJET™ plasmid miniprep kit (Fermentas GmbH) is used according to the manufacturer's instructions.

The plasmids are then characterized by restriction analysis and sequencing. The correct integration of the PcSLI1-ORF into the linearized vector yields the 8.9 kb plasmid pCS.425.ATF1 (Seq ID No. 8), in which the PcATF1-ORF is under control of the shortened HXT7$^{392-1}$ promoter fragment and the CYC1 terminators from S. cerevisiae. This arrangement enables constitutive overexpression of PcATF1 in S. cerevisiae.

For the simultaneous overexpression of PcSLI1 and PcATF2, the two plasmids pCS.426.SLI1 (Seq ID No. 7) and pCS.425.ATF1 (Seq ID No. 8) are then cotransformed into the S. cerevisiae strain 10480-2C, for which once again the method of Gietz and Schiestl (Nat Protoc 2: 31-34 (2007)) is followed. Transformants are selected on synthetic minimal medium (0.16% w/v yeast nitrogen base, 0.5% w/v ammonium sulfate, 2% w/v glucose, 2% w/v agar). For comparison purposes, the two starting plasmids p425HXT7-6HIS (Seq ID No. 5) and p426HXT7-6HIS (Seq ID No. 6) are also cotransformed into the strain RH2754. Next, the transformants are cultured in liquid TAPS medium in order to investigate the effect of the simultaneous over-expression of PcSLI1 and PcATF1 on the production of acetylated sphingoid bases. The transformants are grown aerobically at 30° C. on a rotating shaker at 200-250 rpm. The cells are firstly grown as a preculture in 5 ml TAPS and on reaching the stationary growth phase are used for the inoculation of 20 ml TAPS medium ($\hat{=}$ main culture). Culturing, processing of the samples and procedures for the determination of the production of acetylated sphingoid bases are effected analogously to the previous example.

In the case of the yeast strain transformed with the two plasmids pCS.426.SLI1 and pCS.425.ATF1, the analysis shows a markedly increased titer of tetraacetyl-phytosphingosine compared to the strain transformed with the two control plasmids (p425HXT7-6HIS and p426HXT7-6HIS). This is unambiguous evidence that the simultaneous overexpression of PcSLI1 and PcATF1 in Saccharomyces cerevisiae effects a complete acetylation of the metabolite phytosphingosine.

The invention claimed is:

1. An isolated nucleic acid having a sequence selected from:
   a sequence with at least 90% identity to SEQ ID NO: 1 and comprising at least one substitution, addition and/or deletion relative to SEQ ID NO: 1, wherein said sequence encoding a protein which is capable of converting phytosphingosine to triacetylphytosphingosine by transfer of the acetyl residues from three molecules of acetyl coenzyme A, and a sequence which hybridizes with SEQ ID NO: 1 under stringent conditions,
wherein said stringent conditions include incubation at 68 degrees Celsius in 2× Saline-Sodium Citrate (SSC) Buffer or incubation at 65 degrees Celsius in 7% sodium dodecyl sulfate (SDS), 1% bovine serum albumin (BSA), 1 mM Ethylenediaminetetraacetic acid (EDTA) and 250 mM sodium phosphate buffer and washing at 65 degrees Celsius with 0.2×SSC and 0.1% SDS, and
wherein said sequence codes for a protein which is capable of converting phytosphingosine to triacet¥lphytosphingosine by transfer of the acetyl residues from three molecules of acetyl coenzyme A.

2. An isolated nucleic acid having a sequence selected from:
   a sequence with at least 90% identity to SEQ ID NO: 3 and comprising at least one substitution, addition and/or deletion relative to SEQ ID NO: 3, wherein said sequence encoding a protein which is capable of converting phytosphingosine to triacetylphytosphingosine by transfer of the acetyl residues from three molecules of acetyl coenzyme A; or
   a sequence which hybridizes with SEQ ID NO: 3 under stringent conditions, wherein said stringent conditions include incubation at 68 degrees Celsius in 2× Saline-Sodium Citrate (SSC) Buffer or incubation at 65 degrees Celsius in 7% sodium dodecyl sulfate (SDS), 1% bovine serum albumin (BSA), 1 mM Eth¥lenediaminetetraacetic acid (EDTA) and 250 mM sodium phosphate buffer and washing at 65 degrees Celsius with 0.2×SSC and 0.1% SDS, and wherein said sequence codes for a protein which is capable of converting phytosphingosine to triacetylphytosphingosine by transfer of the acetyl residues from three molecules of acetyl coenzyme A.

3. A genetically modified cell, the genetic modification comprising the introduction of one or more expression vectors comprising the nucleic acid sequence of claim 1 or claim 2 resulting in increased expression at least one enzyme comprising:
   the polypeptide sequence of SEQ ID NO: 2; or
   the polypeptide sequence of SEQ ID NO: 4.

4. The genetically modified cell of claim 3, wherein said genetic modification results in increased expression of the enzyme of SEQ ID NO: 2 and the enzyme of SEQ ID NO: 4.

5. The genetically modified cell of claim 3 or 4, selected from *Saccharomyces cerevisiae, Kluyveromyces lactis, Hansenula polymorpha, Pichia pastoris, Pichia ciferrii, Yarrowia lipolytica, Candida albicans, Candida utilis* and *Ashbya gossypii*.

6. A method for the production of sphingoid bases and/or sphingolipids, comprising the steps of:
   a) contacting the genetically modified cell of claim 3 with a medium containing a carbon source,
   b) culturing the cell under conditions which enable the cell to form sphingoid bases and/or sphingolipids from the carbon source and
   c) optionally isolating the sphingoid bases and/or sphingolipids formed.

7. A method for the production of N-acetylated, primary aliphatic amines, comprising the steps of:
   A) providing at least one enzyme selected from an enzyme E1 with a polypeptide sequence in which up to 10% of the amino acid residues are modified compared to SEQ ID NO: 2 by substitution, addition and/or deletion, wherein said enzyme $E_1$ possesses at least 10% of the enzymatic activity of the enzyme set forth in SEQ ID NO: 2, and wherein said enzymatic activity for enzyme $E_1$ comprises the ability to convert phytosphingosine to triacetylphytosphingosine by transfer of the acetyl residues from three molecules of acetyl coenzyme A, and
   an enzyme $E_2$ with a polypeptide sequence in which up to 10% of the amino acid residues are modified compared to SEQ ID NO: 4 by substitution, addition and/or deletion, wherein said enzyme $E_2$ possesses at least 10% of the enzymatic activity of the enzyme set forth in SEQ ID NO: 4, and wherein said enzymatic activity for enzyme $E_2$ comprises the ability to convert phytosphingosine to triacetylphytosphingosine by transfer of the acetyl residues from three molecules of acetyl coenzyme A,
   B) contacting said at least one enzyme with a medium containing a primary aliphatic amine and acetyl CoA, and
   C) optionally isolating the acetylated amines formed.

* * * * *